United States Patent [19]
Peet et al.

[11] Patent Number: 5,691,368
[45] Date of Patent: Nov. 25, 1997

[54] SUBSTITUTED OXAZOLIDINE CALPAIN AND/OR CATHEPSIN B INHIBITORS

[75] Inventors: Norton P. Peet, Cincinnati; Shujaath Mehdi, West Chester; Matthew D. Linnik, Cincinnati; Michael R. Angelastro, Mason, all of Ohio; Hwa-Ok Kim, Bellevue, Wash.

[73] Assignee: Hoechst Marion Roussel, Inc., Cincinnati, Ohio

[21] Appl. No.: 552,139

[22] Filed: Dec. 11, 1995

Related U.S. Application Data

[63] Continuation-in-part of Ser. No. 371,192, Jan. 11, 1995.

[51] Int. Cl.$^6$ .................................................. A61K 31/42
[52] U.S. Cl. ..................... 514/376; 548/228; 514/236.8; 514/340; 544/137; 546/271.4; 930/250; 530/332
[58] Field of Search ........................... 548/228; 514/376

[56] References Cited

U.S. PATENT DOCUMENTS

| | | | |
|---|---|---|---|
| 3,867,364 | 2/1975 | Umezawa et al. | |
| 4,277,395 | 7/1981 | Bey et al. | 564/159 |
| 4,401,594 | 8/1983 | Umezawa et al. | |
| 4,535,167 | 8/1985 | Freidinger | 548/228 |
| 4,820,691 | 4/1989 | Patel | 514/19 |
| 4,845,079 | 7/1989 | Luly et al. | 514/18 |
| 4,851,387 | 7/1989 | Koike et al. | 514/17 |
| 4,990,525 | 2/1991 | Young et al. | 514/381 |
| 5,081,284 | 1/1992 | Higuchi et al. | 560/159 |
| 5,091,575 | 2/1992 | Luly et al. | 560/115 |
| 5,142,056 | 8/1992 | Kempe et al. | 546/265 |
| 5,214,129 | 5/1993 | Luly et al. | 530/331 |
| 5,294,720 | 3/1994 | Jadhav et al. | 546/265 |
| 5,416,104 | 5/1995 | Hanson et al. | 514/376 |
| 5,444,042 | 8/1995 | Bartus et al. | 514/2 |
| 5,496,927 | 3/1996 | Kolb et al. | 530/328 |
| 5,510,531 | 4/1996 | Higuchi et al. | 564/159 |

FOREIGN PATENT DOCUMENTS

| | | |
|---|---|---|
| 0275101 | 7/1988 | European Pat. Off. |
| 0329295 | 8/1989 | European Pat. Off. |
| 0363284 | 10/1989 | European Pat. Off. |
| 0434365 | 6/1991 | European Pat. Off. |
| 0487980 | 11/1991 | European Pat. Off. |
| 0520336 | 12/1992 | European Pat. Off. |
| 0525420 | 2/1993 | European Pat. Off. |
| 0529568 | 3/1993 | European Pat. Off. |
| 0580161 | 1/1994 | European Pat. Off. |
| 0603769 | 6/1994 | European Pat. Off. |
| 0611756 | 8/1994 | European Pat. Off. |
| 62-279525 | 11/1987 | Japan . |
| 8400365 | 2/1984 | WIPO . |
| 8805050 | 7/1988 | WIPO . |
| 9000399 | 1/1990 | WIPO . |
| 9211850 | 7/1992 | WIPO . |
| 9212140 | 7/1992 | WIPO . |
| 9500535 | 1/1995 | WIPO . |
| 9509838 | 4/1995 | WIPO . |

OTHER PUBLICATIONS

Saito, et al., *Agric Biol Chem* 51, 861–868 (1987).
Ogura, et al., *Agric Biol Chem* 49, (3) 799–805, (1985).
Chemical Abstracts 100:19717u, vol. 100 (1984).
Smith, et al., *Biochemistry* 27, 6568–6573, (1988).
Saito, et al., *Proc. Natl. Acad. Sci. USA*, vol. 90, pp. 2628–2632, Apr. (1993).
Hong, et al., *Stroke*, vol. 25, No. 3, Mar. (1994).
Thompson, et al., *Biochemistry*, vol. 18, No. 8, 1552–1558, (1979).
Minami, et al., *J. Neurosurg* 76:111–118, (1992).
del Cerro, et al., *Neuroscience Letters*, 167, 149–152, (1994).
Caner, et al., *Brain Research*, 607, 354–356, (1993).
Siman, et al., *The Journal of Neuroscience*, 9(5):1579–1590, (1989).
Mehdi, et al., *Bioch & Biophy Res. Communications*, vol. 157, No. 3, (1988).
Mehdi, *TIBS* 16, Apr. 1991.
Saido, et al., *FASEB* 8:814–822 (1994).
Bundgaard, Hans, "Design of Bioreversible Drug Derivatives and the Utility of the Double Prodrug Concept", *Bioreversible Carriers In Drug Design Theory and Application*, Chapter 2, pp. 62–65 (1987).
Raddatz et al, "Renin Inhibitors Containing New P1-P1' Dipeptide mimetics with Heterocycles in P1'", *J. Med. Chem.*, vol. 35, No. 19, 1992 pp. 3525–3536.
Peet et al, Synthesis of Peptidyl Fuuoromethyl Ketones and Peptidyl α–Keto Esters as Inhibitors of Procine Pancreatic Elastase, Human Neutrophil Elastase, and Rat and Human Neutrophil Cathepsin, G, *J. Med Chem*, 1990, 33, pp. 394–407.
Angelastro et al, *J. Org. Chem.* 54, pp. 3913–3916, (1989).
Mehdi, *Bioorganic Chemistry*, 21, pp. 249–259 (1993).
Angelastro et al, *Bioorganic & Medicinal Chemistry Letters*, vol. 2, No. 10, pp. 1235–1238 (1992).
*J. Med. Chem.* 33, pp. 11–13 (1990) "Communications to the Editor".
Minami, et al., "Effects of Inhibitors of Protein Kinase C and calpain in experimental delayed cerebral vasospasm", *J Neurosurg* 76:111–118, (1992).
del Cerro, et al., "Stimulation of NMDA receptors activates calpain in cultured hippocampal slices", *Neuroscience Letters*, 167, 149–152, (1994).
Caner, et al., "Attenuation of AMPA-induced neurotoxicity by a calpain inhibitor", *Brain Research*, 607, 354–356, (1993).
Siman, et al., "Calpain I Activation is Specifically Related to Excitatory Amono Acid Induction of Hippocampal Damage", *The Journal of Neuroscience*, 9(5):1579–1590, (1989).

(List continued on next page.)

*Primary Examiner*—Donald G. Daus
*Attorney, Agent, or Firm*—Michael J. Sayles

[57] ABSTRACT

This invention relates to oxazolidine inhibitors of calpain and/or cathepsin B and to compositions containing them. As inhibitors of calpain and/or cathepsin B, the compounds are useful in the treatment of patients afflicted with acute or chronic neurodegenerative disorders.

16 Claims, No Drawings

OTHER PUBLICATIONS

Mehdi, et al., "Inhibition of the Proteolysis of Rat Erythrocyte Membrane Proteins by a Synthetic Inhibitor of Calpain", *Biochemical and Biophysical Research Communications*, vol. 157, No. 3, (1988).

Mehdi, "Cell-Penetrating Inhibitors of Calpain", *TIBS* 16, Apr. 1991.

Saido, et al., "Calpain: new perspectives in molecular diversity and physiological-pathological involvement", *FASEB* 8:814-822 (1994).

Derwent Abst. 84-129431 (1984) Abstract Japan 58-164563A (1982).

Saito, et al., "Purification and structure of Novel Systeine Proteinase Inhibitors, Staccopins P1 and P2 from Staphylococcus tanabeensis", *Agric Biol Chem* 51, 861-868, (1987).

Ogura, et al., "Purification and Structure of a Novel Cysteine Proteinase Inhibitor, Strepin P-1", *Agric Biol Chem* 49, (3) 799-805, (1985).

Chemical Abstracts 100:19717u, vol. 100 (1984).

Smith, et al., "Inhibition of Cathepsin B By Peptidyl Aldehydes and Ketones: Slow-Binding Behavior of a Trifluoromethyl Ketone", *Biochemistry* 27, 6568-6573, (1988).

Saito, et al., "Widespread activation of caldium-activated neutral proteinase (calpain) in the brain in Alzheimer disease: A potential molecular basis for neuroal degeneration", *Proc. Natl. Acad. Sci. USA*, vol. 90, pp. 2628-2632, Apr. (1993).

Hong, et al., "Neuroprotection with a Calpain Inhibitor in a Model of Focal Cerebral Ischemia", *Stroke*, vol. 25, No. 3, Mar. (1994).

Thompson, et al., "Reaction of Peptide Aldehydes with Serine Proteases. Implications fo rhte Entropy Changes Associated with Enzymatic Catalysis", *Biochemistry*, vol. 18, No. 8, 1552-1558, (1979).

Mehdi, S., *TIBS* 16, pp. 150-153 (Apr. 1991).

Brorson, J., et al, *Stroke*, vol. 20, No. 7, pp. 1259-1267 (Jul. 1995).

Longa, E.Z., et al, *Stroke*, vol. 20, No. 1, pp. 84-91 (Jan. 1989).

Wang, K., Developing selective inhibitors of calpain; *TIPS*, Apr. 1990, vol. 11, pp. 139-142.

Hong et al, *Stroke*, vol. 25, No. 3 (Mar. 1994) pp. 663-669.

Peptides, Structure & Function, (Deber, C.M., et al), Proceedings of the American Peptide Symposium, Hori, H. et al, pp. 819-822, (1985).

Peptides, Structure & Function-Proceedings of the American Peptide Symposium (1985), Galpin, I.J. et al, pp. 799-802 Onyl pp. 799,801.

Zhaozhao Li et al, *J. Med. Chem*, 1993, 36, pp. 3472-3480.

Isabel Charles et al, *J.C.S, Perkin I*, 1980, pp. 1139-1146.

SUBSTITUTED OXAZOLIDINE CALPAIN AND/OR CATHEPSIN B INHIBITORS

This is a continuation-in-part of application Ser. No. 08/371,192, filed Jan. 11, 1995.

BACKGROUND OF THE INVENTION

Neurological damage resulting from a compromise of the cerebrovascular supply is a leading cause of death and disability. With regard to the etiology of ischemic neuronal death, it has been submitted that the sustained elevation of intracellular calcium triggers a variety of intracellular events that can impair or harm cellular function; Hong, Seung-Chyul, et al., Stroke, 25,663–669 (1994); Siesjö, B. K., et al., J. Cereb. Blood Flow Metab., 9, 127–140 (1989); Siesjö, B. K., J. Neurosurg., 77, 169–184 (1992). Under physiological conditions, the precise maintenance of intracellular calcium levels is carefully regulated. The loss of calcium homeostasis and the increase in intracellular calcium during ischemia permits the inappropriate activation of several calcium-sensitive mechanisms, which then become detrimental to cellular function. A prime example of a mechanism of this type is calcium-activated proteolysis. Continuous stimulation of calcium-activated neutral proteases, known as calpains, during ischemia results in the abnormal proteolysis of substrate proteins; Seubert, P., et al., Brain Res., 492, 366–370 (1989); Inuzuka, T., et al., Stroke, 21, 917–922 (1990); Lee, K. S., Proc. Natl. Acad. Sci. U.S.A., 88, 7233–7237 (1991).

Preferred substrates for calpain include cytoskeletal proteins such as microtubule-associated protein 2 (MAP2), spectrin, and neurofilament proteins. Other substrates include key regulatory enzymes such as protein kinase C and calcium/calmodulin-dependent protein kinase II. Said cytoskeletal proteins are degraded and the amount of said regulatory enzymes are reduced following ischemic episodes. Clearly, the uncontrolled proteolysis of any or all of these structural and regulatory proteins can severely impact cellular viability. Thus, inhibitors of calcium-activated proteolysis serve a useful therapeutic function in ischemic cell damage.

Recently, the dipeptidyl aldehyde, Cbz-Val-Phe-H, has been demonstrated to be a cell-penetrating inhibitor of calpain, exhibiting a low $K_i$ for calpain in both broken membrane preparations and intact cell systems; Mehdi, S., Trends Biochem. Sci., 16, 150–153 (1991). Cbz-Val-Phe-H is also useful for inhibiting cathepsin B in patients; European Patent Application OPI No. 0363284 with a publication date of Apr. 11, 1990, inventors Bey, P., et al. Moreover, rats treated with Cbz-Val-Phe-H exhibit significantly smaller volumes of cerebral infarction than saline-treated or vehicle-treated control animals. Intravenous injections of cumulative doses of 30 mg/kg or 60 mg/kg of Cbz-Val-Phe-H were effective in reducing infarction, edema, and calcium-activated proteolysis. The proteolytic response to post-decapitation ischemia was also reduced by Cbz-Val-Phe-H; Hong, Seung-Chyul, et al., Stroke, 25, 663–669 (1994).

Applicants have discovered substitued oxazolidine derivatives of Cbz-Val-Phe-H having a low $K_i$ for calpain as well as cathepsin B while exhibiting good cell penetrating abilities. It is an object of the present invention to provide therapeutic agents for inhibiting calpain and/or cathepsin B in a patient in need thereof. It is a further object of the invention to provide therapeutic agents in the treatment of patients afflicted with an acute or chronic neurodegenerative disorder.

SUMMARY OF THE INVENTION

The present invention relates to compounds having the following general formula (I):

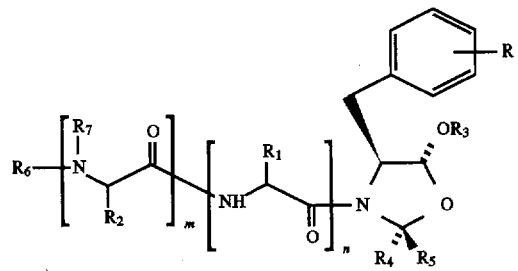

wherein

R and Q are each independently hydrogen, OH, $C_1$–$C_4$ alkyl, $C_1$–$C_4$ alkoxy, $NO_2$, $NH_2$ or halogen;

$R_1$ and $R_2$ are each independently $C_1$–$C_4$ alkyl;

$R_3$ is hydrogen, $C_1$–$C_8$ alkanoyl,

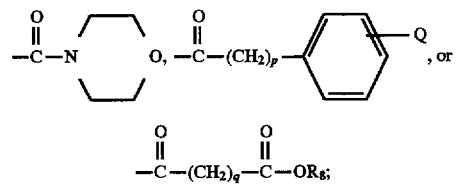

$R_4$ and $R_5$ are each independently hydrogen, $C_1$–$C_4$ alkyl or benzyl;

$R_6$ is t-butyloxycarbonyl, carbobenzyloxy,

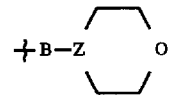

or wherein

Z is N or CH; and

B is a group of the formulae

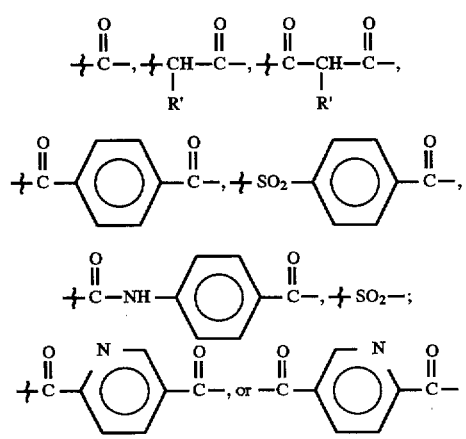

wherein R' is hydrogen or a $C_1$–$C_6$ alkyl group;

$R_7$ is hydrogen or methyl;

$R_8$ is $C_1$–$C_4$ alkyl;

m is the integer zero or one;

n is the integer zero or one;

p is the integer zero to three; and q is the integer zero to three;

and the pharmaceutically acceptable salts thereof. The compounds of formula (I) are calpain and/or cathepsin B inhibitors and are therefore useful in the treatment of acute or chronic neurodegenerative disorders such as ischemic stroke (thrombotic or embolic in origin), hemmorhagic stroke and subsequent vascular phemomena, myocardial infarction, neurologic consequences of coronary bypass and grafting operations, head trauma, Alzheimer's Disease, age-associated dementia, vascular dementias, Parkinson's disease, amyotrophic lateral sclerosis, and the like.

DETAILED DESCRIPTION OF THE INVENTION

As used herein the term "$C_1$–$C_4$ alkyl" refers to a saturated straight or branched chain hydrocarbon radical of one to four carbon atoms. Included within the scope of this term are methyl, ethyl, n-propyl, isopropyl, n-butyl, isobutyl and the like. The term "$C_1$–$C_4$ alkoxy" refers to an alkoxy radical made up of an oxygen radical bearing a saturated straight or branched chain hydrocarbon radical of one to four carbon atoms. Included within the scope of this term are methoxy, ethoxy, propoxy, n-butoxy, isobutoxy, sec-butoxy, t-butoxy and the like. The term "$C_1$–$C8$ alkanoyl" includes formyl, acetyl, propionyl, butyryl, pentanoyl, hexanoyl, 2-ethylhexanoyl and the like. The terms "halo", "halogen" or "halide" refers to a fluorine, chlorine, bromine or iodine atom.

The terms "Ts" or "tosylate" refers to a p-toluenesulfonate functionality of the formula:

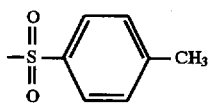

The term "Bn" refers to a benzyl functionality of the formula;

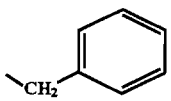

The terms "CBz" or "carbobenzyloxy" refer to a carbobenzyloxy functionality of the formula;

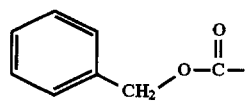

The terms "BOC" or "t-butyloxycarbonyl" refer to t-butyloxycarbonyl functionality of the formula;

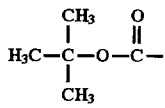

The term "stereoisomers" is a general term for all isomers of individuals molecules that differ only in the orientation of their atoms in space. It includes mirror image isomers (enantiomers), geometric (cis/trans) isomers, and isomers of compounds with more than one chiral center that are not mirror images of one another (diastereomers). For amino acids, the designations L/D, or R/S can be used as described in IUPAC-IUB joint Commission on Biochemical Nomenclature, *Eur. J. Biochem.* 138:9–37 (1984).

The term "pharmaceutically acceptable salt" refers to those salts that are not substantially toxic at the dosage administered to achieve the desired effect and do not independently possess significant pharmacological activity. The salts included within the scope of this term are hydrobromide, hydrochloride, sulfuric, phosphoric, nitric, formic, acetic, propionic, succinic, glycolic, lactic, malic, tartaric, citric, ascorbic, α-ketoglutaric, glutamic, aspartic, maleic, hydroxymaleic, pyruvic, phenylacetic, benzoic, p-aminobenzoic, anthranilic, p-hydroxybenzoic, salicyclic, hydroxyethanesulfonic, ethylenesulfonic, halobenzenesulfonic, toluenesulfonic, naphthalenesulfonic, methanesulfonic, sulfanilic, and the like.

The natural amino acids utilized within the specification contain a chiral carbon atom. Unless otherwise specifically indicated, the preferred compounds utilize the optically active amino acids of the L-configuration; however, applicants contemplate That the amino acids used can also be in the D-configuration. In addition, the compounds of formula (I) wherein m and n are both the integer one can be mixtures of the D- and L-isomers, including racemic mixtures. Examples of the recognized abbreviations for the α-amino acids included within the scope of the specification are set forth in Table 1.

TABLE 1

| AMINO ACID | SYMBOL |
|---|---|
| Alanine | Ala |
| Isoleucine | Ile |
| Leucine | Leu |
| Glycine | Gly |
| Valine | Val |
| Norvaline | Nva |
| Norleucine | Nle |
| Phenylalanine | Phe |
| Tyrosine | Tyr |
| p-Chlorophenylalanine | p-Cl-Phe |
| p-Nitrophenylalanine | p-$NO_2$-Phe |
| p-$NH_2$-Phenylalanine | p-$NH_2$-Phe |

Starting material required for preparation of compounds of formula (I) wherein $R_6$ is t-butyloxycarbonyl, carbobenzyloxy, or

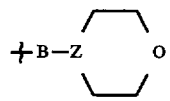

wherein the substituents are as previously described, are commercially available or are readily prepared by one of ordinary skill in the art. For example, the intermediates of the formula

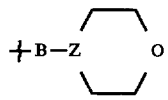

wherein

Z is as previously defined and B is $$+\overset{O}{\underset{\|}{C}}-,\ +CH-\overset{O}{\underset{\|}{C}}-,\ +\overset{O}{\underset{\|}{C}}-CH-\overset{O}{\underset{\|}{C}}-,$$
$$\phantom{+\overset{O}{\underset{\|}{C}}-,\ }\underset{R'}{|}\phantom{-\overset{O}{\underset{\|}{C}}-,\ +\overset{O}{\underset{\|}{C}}-}\underset{R'}{|}$$

$$+\overset{O}{\underset{\|}{C}}-\!\!\bigcirc\!\!-\overset{O}{\underset{\|}{C}}-,\ +SO_2-\!\!\bigcirc\!\!-\overset{O}{\underset{\|}{C}}-,$$

$$+\overset{O}{\underset{\|}{C}}-NH-\!\!\bigcirc\!\!-\overset{O}{\underset{\|}{C}}-,\ +SO_2-;$$

are disclosed in European Patent Application OPI No. 0529568, inventors Peet et al., with a publication date of Mar. 3, 1993. Furthermore, the intermediates of the formula (structure: pyridine ring with –C(O)– on one side and –C(O)–N(morpholine) on the other)

may be prepared as described in Scheme I. All the substituents, unless otherwise indicated, are previously defined. The reagents and starting materials are readily available to one of ordinary skill in the art.

Scheme I (1) H$_3$CO–C(O)–[pyridine]–C(O)–OH $\xrightarrow{\text{Acid chloride Formation, Step A}}$ (2) H$_3$CO–C(O)–[pyridine]–C(O)–Cl $\xrightarrow[\text{Step B}]{\text{Amidation, H–N(morpholine)}}$ (3) H$_3$CO–C(O)–[pyridine]–C(O)–N(morpholine) $\xrightarrow{\text{Hydrolysis, Step C}}$ (4) HO–C(O)–[pyridine]–C(O)–N(morpholine)

Scheme I provides a general synthetic procedure for preparing the appropriate intermediates of the formula (structure: pyridine ring with –C(O)– and –C(O)–Z–O morpholine-like ring)

wherein

Z is as previously defined.

In step A, the carboxylic acid functionality of the appropriate 2,5-pyridinedicarboxylic acid, 2-methyl ester (1) (*Nippon Kagaku Zasshi*, 1967, 88, 563) is converted to its acid chloride using techniques and procedures well known and appreciated by one of ordinary skill in the art, using a reagent such as thionyl chloride, to provide the corresponding 6-carbomethoxynicotinoyl chloride (2).

In step B, the acid chloride (2) is amidated with morpholine by techniques and procedures well known and appreciated by one of ordinary skill in the art to provide the corresponding 5-(morpholine-4-carbonyl)-2-pyridinecarboxylic acid, methyl ester (3).

In step C, the 5-(morpholine-4-carbonyl)-2-pyridinecarboxylic acid, methyl ester (3) is hydrolyzed by techniques and procedures well known and appreciated by one of ordinary skill in the art, with for example, lithium hydroxide in methanol, to give 5-(morpholine-4-carbonyl)-2-pyridine carboxylic acid (4).

In addition, the appropriate intermediate of the formula (structure: pyridine ring with –C(O)– and –C(O)–N(morpholine))

may be prepared as described in Scheme II wherein all substituents are as previously defined. The reagents and starting materials are readily available to one of ordinary skill in the art.

Scheme II (1) H$_3$CO–C(O)–[pyridine]–C(O)–OH $\xrightarrow{\text{Esterification, Step A}}$ (5) H$_3$CO–C(O)–[pyridine]–C(O)–OC(CH$_3$)$_3$ $\xrightarrow[\text{Step B}]{\text{Amidation, H–N(morpholine)}}$ (6) (CH$_3$)$_3$CO–C(O)–[pyridine]–C(O)–N(morpholine) $\xrightarrow{\text{Hydrolysis, Step C}}$ -continued
Scheme II

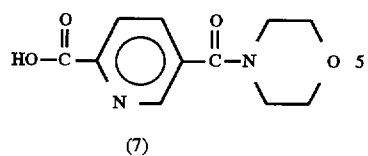

(7)

Scheme II provides a general synthetic procedure for preparing the appropriate intermediates of formula

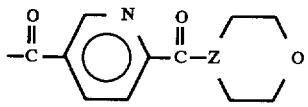

Z is as previously defined.

In step A, the free carboxylic acid functionality of 2,5-pyridinedicarboxylic acid, 2-methyl ester (1) (*Nippon Kagaku Zasshi*, 1967, 88, 563) is converted to its t-butyl ester using techniques and procedures well known and appreciated by one of ordinary skill in the art, such as the t-butyl alcohol adduct of dicyclohexylcarbodiimide (*Synthesis*, 1979, 570), to provide the corresponding 2,5-pyridinedicarboxylic acid, 2-methyl ester, 5-t-butyl ester (5).

For example, the 2,5-pyridinedicarboxylic acid, 2-methyl ester (1) is combined with a molar excess of the t-butyl alcohol adduct of dicyclohexylcarbodiimide in an appropriate organic solvent, such as methylene chloride. The reaction is typically conducted at a temperature range of from 0° C. to room temperature and for a period of time ranging from 2–24 hours. The 2,5-pyridinedicarboxylic acid, 2-methyl ester, 5-t-butyl ester (5) is isolated from the reaction mixture by standard extractive methods as is known in the art and may be purified by crystallization.

In step B, the 2,5-pyridinedicarboxylic acid, 2-methyl ester, 5-t-butyl ester (5) is amidated with morpholine to give the corresponding 6-(morpholine-4-carbonyl)nicotinic acid, t-butyl ester (6).

For example, the 2,5-pyridinedicarboxylic acid, 2-methyl ester, 5-t-butyl ester (5) is contacted with a molar excess of morpholine in an appropriate organic solvent, such as tetrahydrofuran. The reaction is typically conducted at a temperature range of from room temperature to reflux and for a period of time ranging from 5 hours to 3 days. The 6-(morpholine-4-carbonyl)nicotinic acid, t-butyl ester (6) is isolated from the reaction mixture by standard extractive methods as is known in the art and may be purified by crystallization.

In step C, the 6-(morpholine-4-carbonyl)nicotinic acid, t-butyl ester (6) is hydrolyzed, with for example, HCl in nitromethane, to give the corresponding, 6-(morpholine-4-carbonyl)nicotinic acid (7).

Starting material for Scheme VI for the preparation of compounds of formula (I) can be prepared as described in Scheme III. All the substituents, unless otherwise indicated, are previously defined. The reagents and starting materials are readily available to one of ordinary skill in the art.

SCHEME III

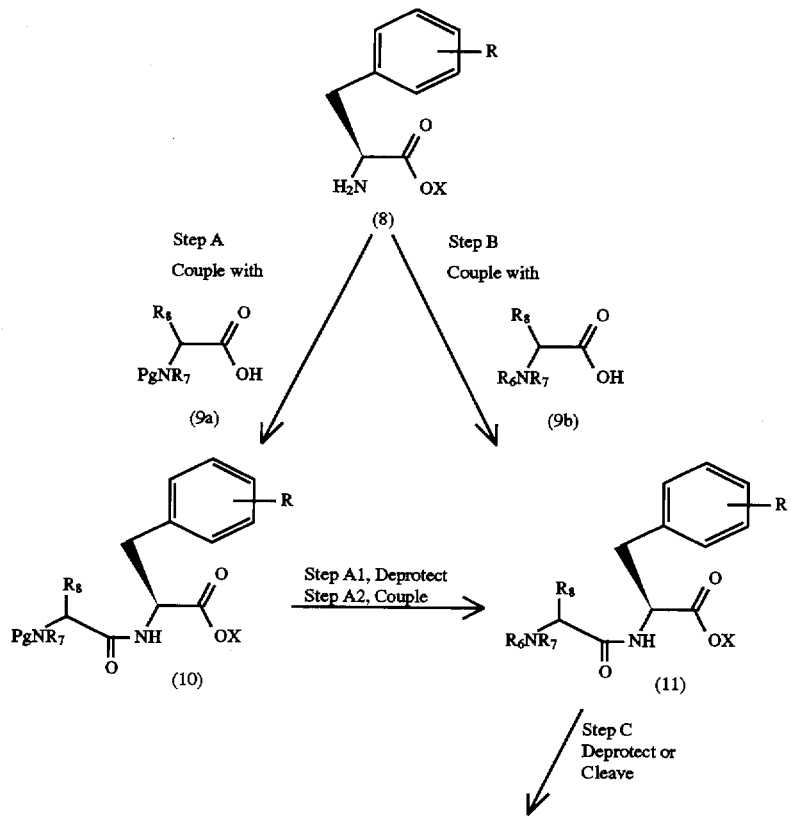

-continued
SCHEME III

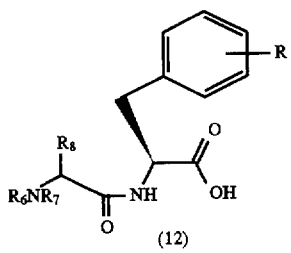

(12)

$R_8 = R_1$ or $R_2$
Pg = protecting group
X = suitable carboxylic acid protecting group or a resin In Scheme III, step A, compounds of structure (8) are coupled with compounds of structure (9a) using standard reactions analogously known in the art, such as those used in peptide synthesis. For example, in an ordinary peptide synthesis, peptides are elongated by deprotecting the α-amine of the N-terminal residue and coupling the next suitably N-protected amino acid through a peptide linkage using the methods described. This deprotection and coupling procedure is repeated until the desired sequence is obtained. This coupling can be performed with the constituent amino acids in stepwise fashion, as depicted in Scheme III, or by condensation of fragments or a combination of both processes, or by solid phase peptide synthesis according to the method originally described by Merrifield, J. Am. Chem. Soc., 1963, 85, 2149–2154, the disclosure of which is hereby incorporated by reference. When a solid phase synthetic approach is employed, the C-terminal carboxylic acid is attached to an insoluble carrier (usually polystyrene). These insoluble carriers form a bond which is stable to the elongation conditions but readily cleaved later. Examples of such carriers are: chloro- or bromomethyl resin, hydroxymethyl resin, and aminomethyl resin. Many of these resins are commercially available with the desired C-terminal amino acid already incorporated.

In addition to the foregoing, peptide synthesis are described in Stewart and Young, "Solid Phase Peptide Synthesis", 2nd ed., Pierce Chemical Co., Rockford, Ill. (1984); Gross, Meienhofer, Udenfriend, Eds., "The Peptides: Analysis, Synthesis, Biology", Vol 1, 2, 3, 5 and 9, Academic Press, New York, 1980–1987; Bodanszky, "Peptide Chemistry: A Practical Textbook", Springer-Verlag, New York (1988); and Bodanszky, et al. "The Practice of Peptide Synthesis", Springer-Verlag, New York (1984), the disclosures of which are hereby incorporated by reference.

Coupling between two amino acids, an amino acid and a peptide, or two peptide fragments can be carried out using standard coupling procedures such as the azide method, mixed carbonic-carboxylic acid anhydride (isobutyl chloroformate) method, carbodiimide (dicyclohexylcarbodiimide, diisopropylcarbodiimide, or water-soluble carbodiimide) method, active ester (p-nitrophenyl ester, N-hydroxy-succinic imido ester) method, Woodward reagent K method, carbonyldiimidazole method, phosphorus reagents such as BOP-Cl, or oxidation-reduction methods. Some of these methods (especially the carbodiimide method) can be enhanced by adding 1-hydroxybenzotriazole. These coupling reactions can be performed in either solution (liquid phase) or solid phase.

The functional groups of the constituent amino acids generally must be protected during the coupling reactions to avoid formation of undesired bonds. The protecting groups that can be used are listed in Greene, "Protective Groups in Organic Chemistry", John Wiley & Sons, New York (1981) and "The Peptides: Analysis, Synthesis, Biology", Vol. 3, Academic Press, New York (198), the disclosure of which is hereby incorporated by reference.

The α-carboxyl group of the C-terminal residue is usually protected by an ester that can be cleaved to give the carboxylic acid. Protecting groups which can be used include: 1) alkyl esters such as methyl and t-butyl, 2) aryl esters such as benzyl and substituted benzyl, or 3) esters which can be cleaved by mild base treatment or mild reductive means such as trichloroethyl and phenacyl esters.

The α-amino group of each amino acid to be coupled to the growing peptide chain must be protected. Any protecting group known in the art can be used. Examples of these protecting groups include: 1) acyl types such as formyl, trifluoroacetyl, phthaloyl, and p-toluenesulfonyl; 2) aromatic carbamate types such as benzyloxycarbonyl (Cbz or Z) and substituted benzyloxycarbonxyls, 1-(p-biphenyl)-1-methylethoxy-carbonyl, and 9-fluorenylmethyloxycarbonyl (Fmoc); 3) aliphatic carbamate types such as tert-butyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycaronbyl; 5) alkyl types such as triphenylmethyl and benzyl; 6) trialkylsilanes such as trimethylsilane; and 7) thiol containing types such as phenylthiocarbonyl and dithiasuccinoyl. The preferred α-amino protecting group is either Boc, Cbz or Fmoc, preferably Boc. Many amino acid derivatives suitably protected for peptide synthesis are commercially available.

The α-amino group protecting group of the newly added amino acid residue is cleaved prior to the coupling of the next amino acid. Conditions for cleavage of such protecting groups are described in Greene, "Protective Groups in Organic Chemistry", Chapter 7, John Wiley & Sons, New York (1981). When the Boc group is used, the methods of choice are trifluoroacetic acid, neat or in dichloromethane, or HCl in dioxane or ethyl acetate. The resulting ammonium salt is then neutralized either prior to the coupling or in situ with basic solutions such as aqueous buffers, or tertiary amines in dichloromethane or dimethylformamide. When the Fmoc group is used, the reagents of choice are piperidine or substituted piperidine in dimethylformamide, but any secondary amine or aqueous basic solutions can be used. The deprotection is carried out at a temperature between 0° C. and room temperature.

Any of the amino acids bearing side chain functionalities must be protected during the preparation of the peptide using any of the above-described groups. Those skilled in the art will appreciate that the selection and use of appropriate protecting groups for these side chain functionalities depends upon the amino acid and presence of other protecting groups in the peptide. The selection of such protecting groups is important in that it must not be removed during the deprotection and coupling of the α-amino group.

For example, when Boc is used as the α-amino protecting group, a benzyl (Bn) ether can be used to protect the hydroxy containing side chains of amino acids such as Tyr, Set or Thr.

When a solid phase synthesis is used, the peptide is cleaved from the resin usually simultaneously with the protecting group removal. When the Boc protection scheme is used in the synthesis, treatment with anhydrous HF containing additives such as dimethyl sulfide, anisole, thioanisole, or p-cresol at 0° C. is the preferred method for cleaving the peptide from the resin. The cleavage of the peptide can also be accomplished by other acid reagents such as trifluoromethanesulfonic acid/trifluoroacetic acid mixtures. If the Fmoc protection scheme is used the N-terminal Fmoc group is cleaved with reagents described earlier. The other protecting groups and the peptide are cleaved from the resin using a solution of trifluoroacetic acid and various additives such as anisole, etc.

More specifically, in Scheme III, step A an α-amino acid of structure (8) wherein X is a suitable α-carboxyl protecting group, such as a methyl ester, is dissolved in a suitable anhydrous organic solvent, such as anhydrous DMF or anhydrous methylene chloride under an inert atmosphere, such as nitrogen. To this solution is added an equivalent of N-hydroxybenzotriazole hydrate, an equivalent of 1-(3-dimethylaminopropyl)-3-ethylcarbodiimide hydrochloride and an equivalent of the protected α-amino acid of structure (9a) dissolved in a suitable anhydrous organic solvent, such as anhydrous DMF or anhydrous methylene chloride. The reaction is then allowed to stir for about 1 to 15 hours. The coupled product of structure (10) is then isolated and purified by techniques well known in the art, such as extractive techniques and flash chromatography. For example, the reaction is diluted with a suitable organic solvent such as ethyl acetate, rinsed with water, dried over anhydrous magnesium sulfate, filtered and concentrated under vacuum. The residue is purified by flash chromatography on silica gel with a suitable eluent, such as ethyl acetate/hexane to provide the coupled product (10).

Alternatively, in Scheme III, step A a suitably protected α-amino acid of structure (9a) is dissolved in a suitable organic solvent under an inert atmosphere, such as nitrogen. Examples of suitable organic solvents are petroleum ethers, a chlorinated hydrocarbon such as carbon tetrachloride, ethylene chloride, methylene chloride, or chloroform; a chlorinated aromatic such as 1,2,4-trichlorobenzene, or o-dichlorobenzene; carbon disulfide; an ethereal solvent such as diethyl ether, tetrahydrofuran, or 1,4-dioxane, or an aromatic solvent such as benzene, toluene, or xylene. Methylene chloride is the preferred solvent for this coupling reaction. The solution is then treated with one to four equivalents of a suitable amine. Examples of suitable amines are tertiary organic amines such as tri-(lower alkyl)amines, for example, triethylamine; or aromatic amines such as picolines, collidines, and pyridine. When pyridines, picolines, or collidines are employed, they can be used in high excess and act therefore also as the reaction solvent. Particularly suitable for the coupling reaction is N-methylmorpholine (NMM). The solution is then cooled to about −20° C. and one equivalent of isobutyl chloroformate is added. The reaction is allowed to stir for about 10 to 30 minutes and 1 to 4 equivalents of the amino acid ester of structure (8) (X is an ester group, such as methyl or ethyl and the amino acid can be an acid addition salt or a free base), is added to the reaction. The reaction is stirred for 30 minutes to 2 hours at about −20° C. and then it is allowed to warm to room temperature and stirred for 1 to 3 hours. The coupled product (10) is then isolated and purified by techniques well known in the art, such as extractive techniques and flash chromatography. For example, the reaction is diluted with a suitable organic solvent such as methylene chloride, rinsed with water, dried over anhydrous magnesium sulfate, filtered and concentrated under vacuum. The residue is purified by flash chromatography on silica gel with a suitable eluent, such as ethyl acetate/hexane to provide the coupled product (10).

In Scheme III, step A1, the protecting group (Pg) on the coupled product (10) is removed under conditions well known in the art, as described by T. W. Green, "Protective Groups in Organic Synthesis", Chapter 7, 1981, John Wiley & Sons, Inc and the primary amine is coupled with $R_6$ to provide the coupled product of structure (11). For example, when Pg is a tert-butyl carbamate (BOC) on the coupled product (10), the compound is dissolved in methanolic hydrochloric acid, stirred for several hours and then concentrated under vacuum. The residue is then dissolved in water, neutralized with saturated sodium bicarbonate and extracted with ethyl acetate. The organic extracts are dried over anhydrous magnesium sulfate, filtered and concentrated under vacuum. The residue is purified by flash chromatography on silica gel with a suitable eluent, such as ethyl acetate/hexane to provide the primary amine.

Alternatively, when Pg is a tert-butyl carbamate (BOC) on the coupled product (10), the compound can be dissolved in trifluoroacetic acid and stirred at room temperature for 1 to 12 hours. The reaction is then poured carefully into water, neutralized with sodium bicarbonate and extracted with ethyl acetate. The combined organic extracts are dried over anhydrous magnesium sulfate, filtered and concentrated under vacuum. The residue can be purified by flash chromatography on silica gel with a suitable eluent, such as ethyl acetate/hexane to provide the primary amine.

In Scheme III, step A2, the above prepared primary amine is coupled to $R_6$ to provide the coupled product (11) under conditions well known in the art. For example, wherein $R_6$ is an acid of structure (9c),

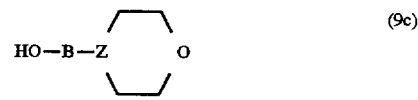

the acid (9c) is subjected to a coupling reaction analogous to the procedures described in Scheme III, step A above. For example, the acid (9c) is dissolved in a suitable organic solvent, such as methylene chloride, under an inert atmosphere, such as nitrogen. The solution is then treated with one to four equivalents of a suitable amine, such as N-methylmorpholine, cooled to about −20° C. and one equivalent of isobutylchloroformate is added. The reaction is allowed to stir for about 10 to 30 minutes and 1 to 4 equivalents of the above prepared primary amine is added to the reaction. The reaction is stirred for 30 minutes to 2 hours at about −20° C. and then it is allowed to warm to room temperature and stir for 1 to 3 hours. The coupled product (11) is then isolated and purified by techniques well known in the art, such as extractive techniques and flash chromatography. For example, the reaction is diluted with a suitable organic solvent such as methylene chloride, rinsed with water, dried over anhydrous magnesium sulfate, filtered and concentrated under vacuum. The residue is purified by flash chromatography on silica gel with a suitable eluent, such as ethyl acetate/hexane to provide the coupled product (11).

Alternatively, the above prepared primary amine is dissolved in a suitable anhydrous organic solvent, such as methylene chloride under an inert atmosphere, such as nitrogen. To this solution is added an equivalent of N-hydroxybenztriazole hydrate, an equivalent of 1-(3-dimethylaminopropyl)-3-ethylcarbodiimide hydrochloride and an equivalent of the acid of structure (9c), dissolved in a suitable anhydrous organic solvent, such as methylene chloride. The reaction is then allowed to stir for about 1 to 15 hours. The coupled product of structure (11) is then isolated and purified by techniques well known in the art, such as extractive techniques and flash chromatography. For example, the reaction is diluted with a suitable organic solvent such as ethyl acetate, rinsed with water, dried over anhydrous magnesium sulfate, filtered and concentrated under vacuum. The residue is purified by flash chromatography on silica gel with a suitable eluent, such as ethyl acetate/hexane to provide the coupled product (11).

The coupled product (11) can also be prepared directly in Scheme III, step B by a coupling reaction of the α-amino acid of structure (8) wherein X is a suitable α-carboxyl protecting group, such as a methyl ester, with the α-amino acid of structure (9b). The α-amino acid (9b) is readily prepared by coupling the $R_6$ substituent to the amino acid of structure (9b')

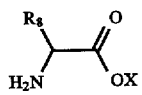

wherein X is a suitable α-carboxyl protecting group, such as a methyl ester, under conditions well known to one of ordinary skill in the art, such as the procedures described in Scheme III, step A. The α-carboxyl protecting group of this coupled product is then removed under conditions well known in the art to provide the α-amino acid of structure (9b). For example, wherein X is a methyl or ethyl group, the compound is dissolved in ethanol, treated with an equal volume of water and an equivalent of lithium hydroxide. The reaction is allowed to stir for 1 to 6 hours. The resulting acid is then isolated by techniques well known in the art. For example, the organic solvent is removed under vacuum and the remaining aqueous solution is acidified with dilute hydrochloric acid. The aqueous is then extracted with a suitable organic solvent, such as ethyl acetate, and the combined organic extracts are dried over anhydrous magnesium sulfate, filtered and concentrated under vacuum to provide the α-amino acid (9b).

In Scheme III, step C, the coupled product (11) is then deprotected or cleaved from the solid phase under conditions well known in the art to provide the acid of structure (12). For example, wherein X is a methyl or ethyl group on structure (11), the compound is dissolved in a suitable organic solvent, such as ethanol and treated with approximately an equal volume of water. To this solution, with stirring is added 1 to 2 equivalents of lithium hydroxide and the reaction is allowed to stir for 1 to 6 hours. The resulting acid is then isolated and purified by techniques well known in the art. For example, the organic solvent is removed under vacuum and the remaining aqueous solution is acidified with dilute hydrochloric acid. The aqueous phase is then extracted with a suitable organic solvent, such as ethyl acetate, and the combined organic extracts are dried over anhydrous magnesium sulfate, filtered and concentrated under vacuum. The residue can then be purified by flash chromatography on silica gel with a suitable eluent, such as methanol/chloroform to provide the acid (12).

Additional starting material for Scheme VI for the preparation of compounds of formula (I) can be prepared as described in Scheme IV. All the substituents, unless otherwise indicated, are previously defined. The reagents and starting materials are readily available to one of ordinary skill in the art.

SCHEME IV

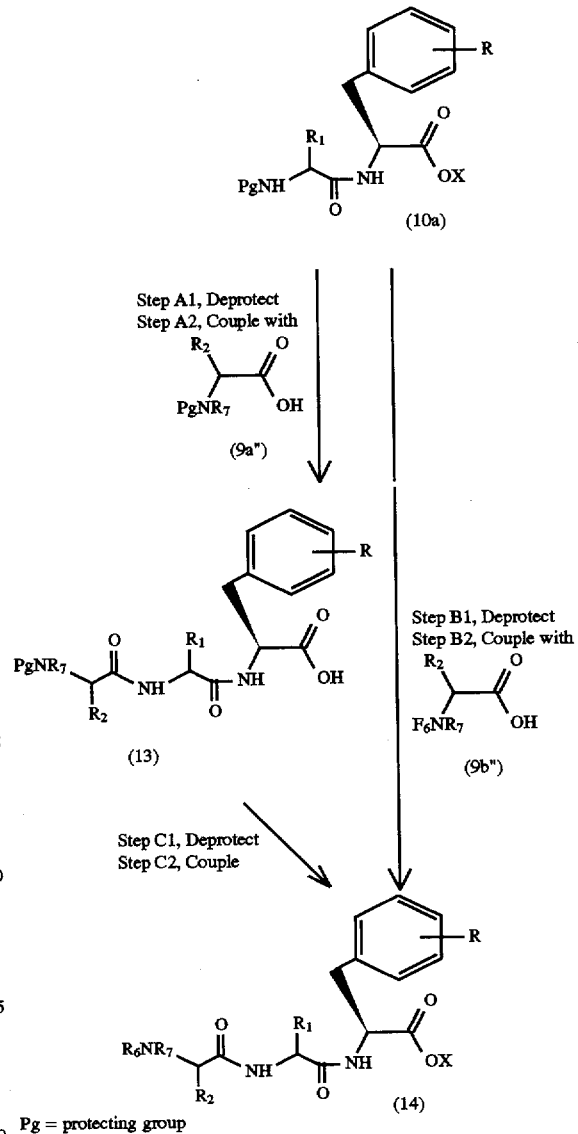

Pg = protecting group
X = suitable carboxyl protecting group or a resin

-continued
SCHEME IV

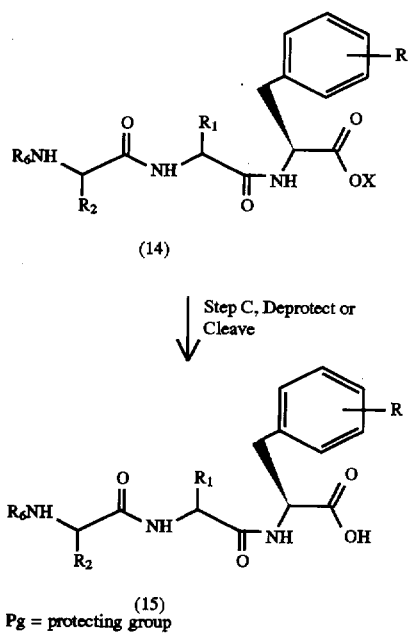

(14)

↓ Step C, Deprotect or Cleave (15)

Pg = protecting group
X = suitable carboxyl protecting group or a resin

In Scheme IV, step A1 the coupled product (10a) [prepared in Scheme III wherein $R_8=R_1$ and $R_7$ is hydrogen] is deprotected to produce the primary amine under conditions analogous to the procedure described in Scheme III, step A1. The resulting primary amine is then subjected to a coupling reaction with the protected α-amino acid of structure (9a') in a manner analogous to the procedures described previously in Scheme III, step A to provide the coupled product (13).

In Scheme IV, step C1 the above prepared coupled product (13) is deprotected to produce the primary amine under conditions analogous to the procedure described in Scheme III, step A1. The resulting primary amine is then subjected to a coupling reaction with $R_6$ in a manner analogous to the procedures described previously in Scheme III, step A to provide the coupled product (14).

Alternatively, the above coupled product (14) may be prepared directly as described in Scheme IV, steps B1 and B2. The coupled product (10a) is deprotected to produce the primary amine under conditions analogous to the procedure described in Scheme III, step A1. The resulting primary amine is then subjected to a coupling reaction with the α-amino acid of structure (9b') [as prepared in Scheme III, wherein $R_8$ is $R_2$] in a manner analogous to the procedures described previously in Scheme III, step A to provide the coupled product (14).

In Scheme IV, step C the above prepared coupled product (14) is deprotected or cleaved from the solid phase under conditions well known in the art, such as that described previously in Scheme III, step C to provide the acid of structure (15).

It is understood that the sequence of the coupling of the amino acids as described in Schemes III and IV is illustrative only and not intended to limit the scope of the present invention in any way. It is appreciated and readily determined by one of ordinary skill in the arc that the coupling sequence as set forth in Schemes III and IV may be altered depending upon the starting material available. For example the substituted or unsubstituted phenylalanine may be the last residue coupled to the chain prior to cyclization in Scheme VI.

Starting material required in Schemes III, IV and VI wherein $R_7$ is methyl can be prepared as described in Scheme V. All the substituents, unless otherwise indicated, are previously defined. The reagents and starting materials are readily available to one of ordinary skill in the art.

Scheme V

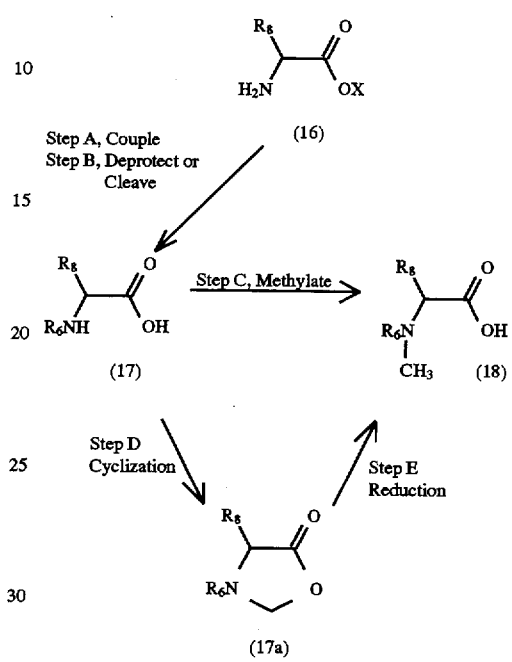

$R_8 = R_1$ or $R_2$
X = a suitable carboxyl protecting group or a resin

In Scheme V, step A an α-amino acid of structure (16) wherein X is a suitable α-carboxyl protecting group, such as a methyl ester, is coupled with $R_6$ in a manner analogous to the procedures described in Scheme III, step A to provide the coupled product.

In Scheme V, step B the coupled product is deprotected or cleaved from the solid phase under conditions well known in the art, such as that described previously in Scheme III, step C to provide the acid of structure (17).

In Scheme V, step C the acid (17) is N-methylated to provide the N-methylated compound of structure (18). For example, the acid (16) is dissolved in a suitable organic solvent, such as tetrahydrofuran, cooled to about 0° C. and treated with excess methyl iodide. Then 1 to 3 equivalents of sodium hydride is added to the solution which is stirred for about 10 minutes at 0° C. and then warmed to room temperature and stirred for 24 to 48 hours. The product is then isolated by techniques well known in the art, such as extractive methods. For example, dilute aqueous hydrochloric acid is added and the reaction is extracted with a suitable organic solvent, such as ethyl acetate. The organic extracts are then combined, washed with 5% sodium thiosulfate, brine, dried over anhydrous magnesium sulfate, filtered through a pad of silica gel and concentrated under vacuum to provide the N-methylated compound (18).

Alternatively, the N-methylated compound (18) can be prepared following the procedure described in Scheme V, steps D and E, from the acid (17).

In Scheme V, step D the acid (17) is cyclized to provide the oxazolidine described by structure (17a). For example, the acid (17) is dissolved in a suitable organic solvent, such as benzene and treated with an excess of paraformaldehyde.

To this is added about 0.2 to 0.4 equivalents of p-toluenesulfonic acid and the reaction is heated at reflux for about 23 hours with continuous removal of water using a Dean-Stark trap. The reaction is then allowed to cool to room temperature and the product is isolated and purified by techniques well known in the art. For example the cooled reaction is concentrated under vacuum, the residue taken up in a suitable organic solvent, such as ethyl acetate, rinsed with saturated sodium bicarbonate, the organic phase dried over anhydrous magnesium sulfate, filtered and concentrated under vacuum. The residue is then purified by flash chromatography on silica gel with a suitable eluent, such as ethyl acetate/hexane to provide the oxazolidine (17a).

In Scheme V, step E the oxazolidine (17a) is reduced under conditions well known in the art to provide the N-methylated compound of structure (18). For example, the oxazolidine (16a) is dissolved in a suitable organic solvent, such as chloroform and treated with excess trifluoroacetic acid. To the solution is added an excess of triethylsilane with stirring at room temperature. The reaction is allowed to stir for 1 to 7 days and then concentrated under vacuum to provide the N-methylated compound (18).

The compounds of formula (I) wherein $R_3$ is hydrogen can be prepared as described in Scheme VI. All the substituents, unless otherwise indicated, are previously defined. Acid (19) in Scheme VI is available to one of ordinary skill in the art, either commercially or for example following generally the procedures set forth in Schemes I through V. The reagents are readily available to one of ordinary skill in the art.

SCHEME VI

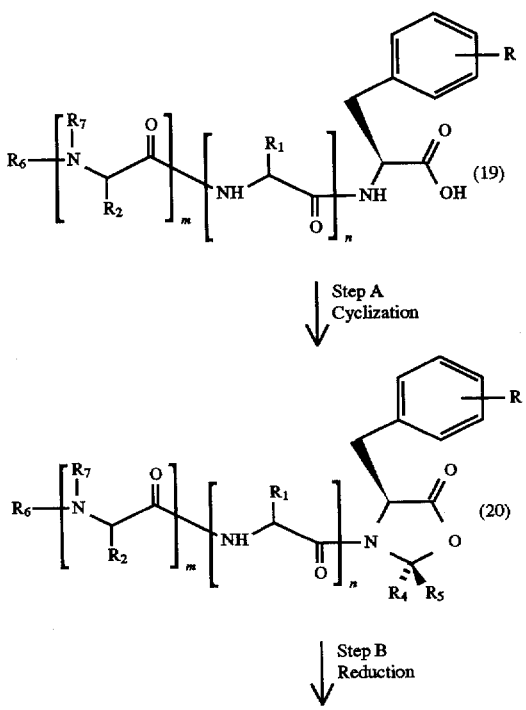

Step B
Reduction

-continued
SCHEME VI

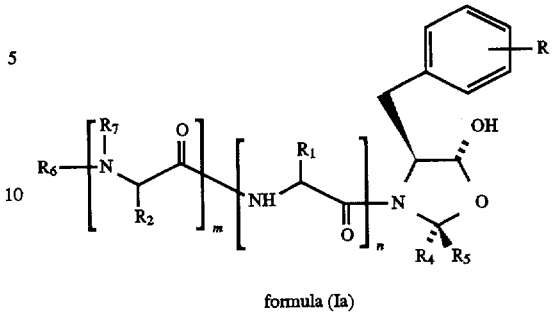

formula (Ia)

In Scheme VI, step A the acid of structure (19) is subjected to a cyclization reaction to provide the oxazolidinone of structure (20). For example, an acid (19) is combined with 0.1 to 0.3 equivalents of p-toluenesulfonic acid and an excess of a ketone or aldehyde of structure

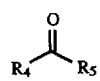

wherein $R_4$ and $R_5$ are each independently hydrogen, aryl, $C_1$–$C_4$ alkyl or benzyl, in a suitable organic solvent. Examples of the above ketone and aldehyde are paraformaldehyde, acetaldehyde, acetone, propionaldehyde, butyraldehyde, isobutyraldehyde, 2-butanone, valeraldehyde, isovaleraldehyde, 2-methylbutyraldehyde, 2-pentanone, 3-pentanone, 2-hexanone, 3-hexanone, 2-methyl-3-pentanone, 3-methyl-2-pentanone, 4-methyl-2-pentanone, 3-heptanone, 4heptanone, 5-nonanone, benzaldehyde, phenylacetaldehyde and the like. Examples of suitable organic solvents are benzene, 1,2-dichloroethane, toluene, and the like. The preferred organic solvent is toluene. An amount of 4A molecular sieves equal to approximately 3 times the weight of the acid (19) may optionally be added to the reaction. The reaction is then heated at reflux for 2 to 24 hours with continuous removal of water via a Dean-Stark trap. The reaction is then cooled to room temperature and concentrated under vacuum. The product is isolated and purified by techniques well known in the art, such as extractive methods and flash chromatography. For example, the residue is dissolved in a suitable organic solvent, such as ethyl acetate, rinsed with saturated sodium bicarbonate, dried over anhydrous magnesium sulfate, filtered and concentrated under vacuum. The product is then purified by flash chromatography on silica gel with a suitable eluent, such as hexane/ethyl acetate to provide the oxazolidinone (20).

In step B, the oxazolidinone (20) is reduced under conditions well known in the art to provide the oxazolidine of formula (Ia). For example, the oxazolidinone (20) is dissolved in a suitable organic solvent, such as toluene and cooled to −78° C. Approximately 2.1 equivalents of a suitable reducing agent, such as diisobutylaluminum hydride is added and the reaction is stirred at −78° C. for 20 minutes to 2 hours. The reaction is then carefully quenched with dilute aqueous hydrochloric acid and the reaction is allowed to warm to room temperature. The product is then isolated and purified by techniques well known in the art such as extractive methods and flash chromatography. For example, the reaction is extracted with a suitable organic solvent, such as ethyl acetate. The combined organic extracts are dried over anhydrous magnesium sulfate, filtered and concentrated under vacuum. The product is then purified by flash chromatography on silica gel with a suitable eluent, such as ethyl acetate/hexane to provide the oxazolidine of formula (Ia).

The compounds of formula (I) wherein $R_3$ is $C_1$–$C_4$ alkanoyl or 4-morpholinecarbonyl can be prepared as described in Scheme VII. All the substituents, unless otherwise indicated, are previously defined. The reagents and starting materials are readily available to one of ordinary skill in the art.

Scheme VII

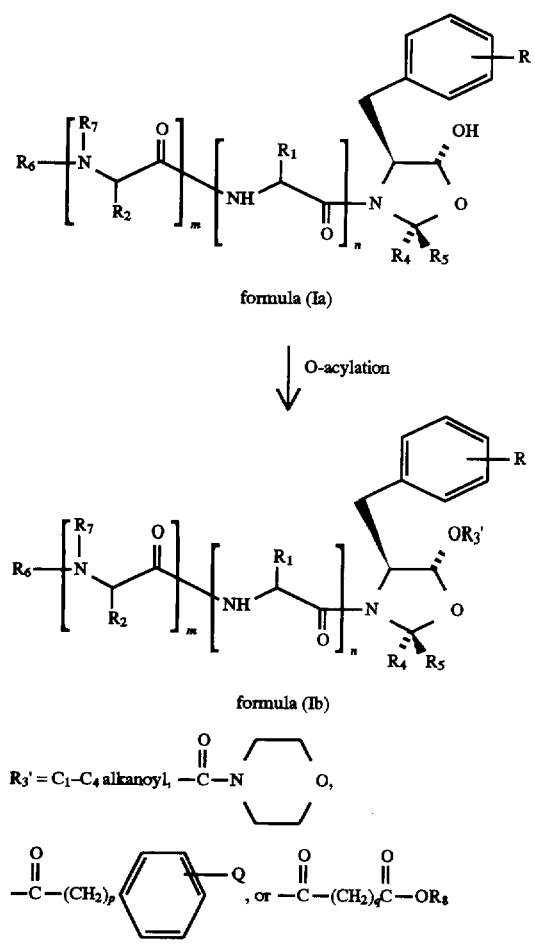

formula (Ia)

↓ O-acylation formula (Ib)

$R_3' = C_1$–$C_4$ alkanoyl,

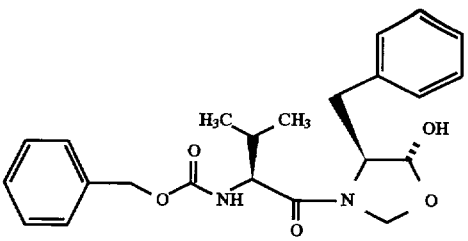

In Scheme VII, the oxazolidine of formula (Ia) is O-acylated under standard conditions well known in the art to provide the O-acylated oxazolidine of formula (Ib). For example, oxazolidine of formula (Ia) is dissolved in a suitable organic solvent, such as methylene chloride and treated with a slight excess of a suitable trialkylamine, such as triethylamine. An excess of an alkylating agent is added at room temperature and the reaction is stirred at room temperature for 1 to 24 hours. Examples of O-acylating agents are acetyl chloride, propionyl chloride, butyryl chloride, isobutyryl chloride, benzoyl chloride, morpholinecarbonyl chloride, methyl succinyl chloride, methyl oxalyl chloride, ethyl oxalyl chloride, 2-ethylhexanoyl chloride, 4-methoxyphenylacetyl chloride and the like. The reaction is then concentrated under vacuum. The product is then isolated and purified by techniques well known in the art, such as extractive methods and flash chromatography. For example, the residue is dissolved in dilute aqueous hydrochloric acid and a suitable organic solvent, such as ethyl acetate. The layers are separated and the aqueous layer extracted with ethyl acetate. The organic layer and organic extract are combined, dried over anhydrous magnesium sulfate, filtered and concentrated under vacuum. The product is purified by flash chromatography on silica gel with a suitable eluent, such as ethyl acetate/hexane to provide the O-acylated oxazolidine of formula (Ib).

The following examples present typical syntheses as described in Schemes I through VII. These examples are understood to be illustrative only and are not intended to limit the scope of the present invention in any way. As used herein, the following terms have the indicated meanings: "g" refers to grams; "mmol" refers to millimoles; "ml" refers to milliliters; "bp" refers to boiling point; "mp" refers to melting point; "° C." refers to degrees Celsius; "mm Hg" refers to millimeters of mercury; "µL" refers to microliters; "µg" refers to micrograms; and "µM" refers to micromolar; "Cbz" means carbobenzyloxy; "DMF" means dimethylformamide; "THF" means tetrahydrofuran; "TBAF" means tetrabutylammonium fluoride; "NMM" means N-methylmorpholine; "DMSO" means dimethylsulfoxide; "HOBT" means hydroxybenzotriazole; "EDC" means 1-(3-dimethylaminopropyl)-3-ethylcarbodiimide hydrochloride.

EXAMPLE 1

Preparation of [4S-[3(R*),4α,5β]]-[1-[[5-hydroxy-4-(phenylmethyl)-3-oxazolidinyl]carbonyl]-2-methylpropyl]-carbamic acid, phenylmethyl ester. (MDL 104,903)

Step A

Scheme VI, step A; Cbz-Val-Phe-OH (4.67 g, 11.7 mmol, obtained from Sigma Chemical Company, St. Louis, Mo. 63178) is combined with paraformaldehyde (5 g) and p-toluenesulfonic acid monohydrate (500 mg, 2.6 mmol) in benzene (120 mL). The reaction is heated at reflux for 23 hours with continuous removal of water with a Dean-Stark trap. The reaction then cooled to room temperature and concentrated under vacuum. The residue is dissolved in ethyl acetate (100 mL) and saturated aqueous sodium bicarbonate (60 ) is added with mixing. The layers are then separated and the aqueous layer is extracted with ethyl acetate (2×50 mL). The organic layer and organic extracts are combined and dried over anhydrous magnesium sulfate, passed through a short pad of silica gel and the filtrate is concentrated under vacuum. The residue is then purified by flash chromatography (hexane/ethyl acetate, 95:5 to 90:10 to 80:20, silica gel) to provide [S-(R*,R*)]-[2-methyl-1-[[5-oxo-4-(phenylmethyl)-3-oxazolidinyl]carbonyl]propyl]-carbamic acid, phenylmethyl ester (2.00 g, 42%) as a foam; $[\alpha]^{20}_D$+113.95 (c 0.55, CHCl$_3$); IR (CHCl$_3$) 3314, 3032, 2934, 1804, 1714, 1659, 1437, 1233 cm$^{-1}$; MS m/z 411 (M+H$^+$), 367, 268, 234, 206, 178, 162, 91.

Anal. Calcd. for $C_{23}H_{26}N_2O_5$: C, 67.31; H, 6.38; N, 6.83; Found C, 67.12; H, 6.51; N, 6.85.

Step B

Scheme VI, step B: The above prepared [S-(R*,R*)]-[2-methyl-1-[[5-oxo-4-(phenylmethyl)-3oxazolidinyl]carbonyl]propyl]-carbamic acid, phenylmethyl ester (1.93 g, 4.7 mmol) is dissolved in toluene (60 mL) and the solution is cooled to −78° C. The solution is then treated with diisobutylaluminum hydride (10 mL, 10 mmol, 1M solution in toluene, DIBAL-H) and the reaction is stirred at −78° C. for 30 minutes. Then 1N HCl (60 mL) is slowly added to the reaction which is subsequently allowed to warm to room temperature. The reaction is extracted with ethyl acetate (3×50 mL). The combined organic extracts are dried over anhydrous magnesium sulfate, passed through a short pad of silica gel and the filtrate is concentrated under vacuum. The residue is then purified by flash chromatography (hexane/ethyl acetate, 95:5 to 90:10 to 80:20 to 60:40, silica gel) to provide the final title compound (640 mg, 33%) as an oil; $[\alpha]^{20}_D$−46.13 (c 0.98, $CHCl_3$); IR (KBr) 3406 (br), 3032, 2964, 1710, 1640, 1529, 1454 $cm^{-1}$; MS m/z 411 (M+H$^+$), 383, 339, 275, 91. Anal. Calcd for $C_{23}H_{28}N_2O_5$: C, 66.98; H, 6.83; N, 6.79; Found C, 66.88; H, 7.07; N, 6.81.

EXAMPLE 2

Preparation of [4S-[3(R*),4α,5β]]-1-[[5-(acetyloxy)-4-(phenylmethyl)-3-oxazolidinyl]carbonyl]-2-methylpropyl]carbamic acid, phenylmethyl ester. (MDL 104,860)

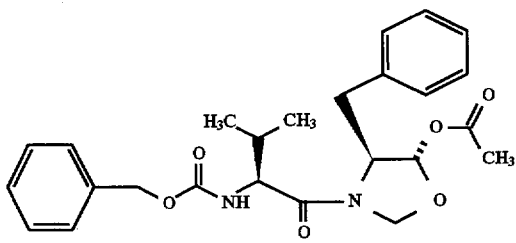

Scheme VII; The title compound prepared in example 1 (250 mg, 0.6 mmol) and triethylamine (0.3 mL) are dissolved in methylene chloride (20 mL). Acetyl chloride (0.3 mL, 4.2 mmol) is then added to the solution at room temperature and the reaction is stirred overnight. The reaction is then concentrated under vacuum and the residue is dissolved in ethyl acetate (30 mL) and 1N HCl (30 mL). The Layers are separated and the aqueous layer is extracted with ethyl acetate (3×30 mL). The organic layer and organic extracts are combined, dried over anhydrous magnesium sulfate, passed through a short pad of silica gel and the filtrate is concentrated under vacuum. The residue is purified by preparative thin layer chromatography (hexane/ethyl acetate, 80:20, silica gel) to provide the title compound (200 mg, 73%) as a sticky oil; $[\alpha]^{20}_D$−36.13 (c 0.64, $CHCl_3$); 1H NMR (300 MHz, $CDCl_3$) δ0.7, 0.89, 1.00 (three d, 6H, J=6.6 Hz each, $CH(CH_3)_2$, rotamers about amide bond), 1.98 and 1.87 (two s, 3H, C(=O)$CH_3$), 2.00 (m, 1H, $CH(CH_3)_2$), 2.73, 2.93 and 3.14 (dd, d, d, 2H, J=13.6, 9.6, 7.1 Hz and 13.8, 3.9 Hz, $CH_2$Ph), 3.89 and 4.01 (two t, 1H, J=8.4, 8.8 Hz, CHCH($CH_3$)$_2$ for valine), 4.43 and 4.77 (dd and t, 1H, J=3.9, 9.5 HZ and 7.4 Hz, CH$CH_2$Ph in oxazolidine ring), 5.00–5.30 (set of m, 4H, O$CH_2$Ph and NCH$_2$O-), 5.34 and 5.53 (two d, 1H, J=9.0, 10.0 Hz, NH), 5.47 and 6.15 (two d, 1H, ratio 1:2.1, J=5.2 and 8.6 Hz, OCHOC(=O)$CH_3$), 7.2–7.5 (set of m, 10H, phenyls); $^{13}C$ NMR (75 MHz, $CDCl_3$) δ171.71 (18.03), 18.97 (19.45), 20.86, 30.93, 35.80 (38.32), 58.08 (58.91), 62.11 (62.28), 66.97 (67.03), 78.38 (78.76), 97.36 (97.92), 156.15 (156.26), 168.66 (169.48), 169.70 (170.89); IR (neat) 3298 (br), 3032, 2965, 1750, 1715, 1651, 1233 $cm^{-1}$; MS m/z 455 (M+H$^+$) 395, 351, 252, 234, 162, 91.

Anal. Calcd for $C_{25}H_{30}N_2O_6$: C, 66.07; H, 6.65; N, 6.16; Found C, 65.76; H, 6.60; N, 6.16.

EXAMPLE 3

Preparation of [4S-[3(R*),4α,5β]]-3-[3-methyl-1-oxo-2-[[(phenylmethoxy)carbonyl]amino]butyl]-4-(phenylmethyl)-5-oxazolidinyl ester, 4-morpholinecarboxylic acid (MDL 105,803).

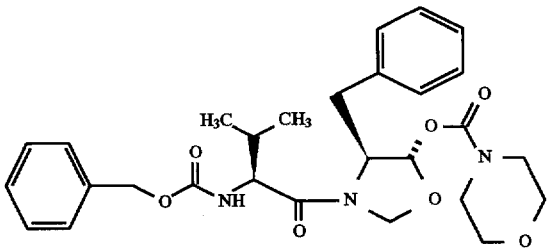

Scheme VII; The title compound prepared in example 1 (243 mg, 0.59 mmol) is dissolved in methylene chloride (30 mL). 4-dimethylaminopyridine (10 mg, DMAP) is added with stirring. Then add triethylamine (0.2 mL, 1.2 mmol) and 4-morpholinecarbonyl chloride (0.1 mL, 0.86 mmol), and stir the reaction at room temperature for approximately 20 hours. Concentrate the reaction under vacuum and dissolve the residue in ethyl acetate (50 mL) and 1N HCl (20 mL). Separate the layers, wash the organic layer with brine (50 mL), dry over anhydrous magnesium sulfate, pass through a short pad of silica gel and concentrate the filtrate under vacuum. Recrystallize the resulting white solids from ethyl acetate/hexane to provide the title compound (200 mg) as a white solid; $[\alpha]^{20}_D$−70.51 (c 0.91 DMSO) IR (KBr) 3302 (br), 3030, 2965, 1717, 1659, 1433, 1242 $cm^{-1}$.

Anal. Calcd for $C_{28}H_{35}N_3O_2$: C, 63.99; H, 6.71; N, 8.00; Found; C, 63.50; H, 6.70; N, 7.93.

EXAMPLE 4

Preparation of [4S-[3(R*),4α,5β]]-[1-[[5-hydroxy-4-(phenylmethyl-3-oxazolidinyl]carbonyl]-2-methylpropyl]methyl-carbamic acid, phenylmethyl ester (MDL 105,423).

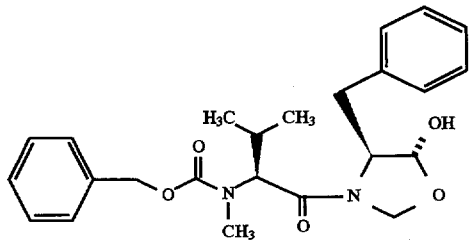

Step A

Scheme V, step D; Combine Cbz-Val-OH (5.0 g, 20 mmol), p-toluenesulfonic acid monohydrate (300 mg) paraformaldehyde (4.0g) in 1,2-dichloroethane (200 mL) and heat at reflux overnight with continuous removal of water via a Dean-Stark trap. Cool the reaction to room temperature and concentrate urine: vacuum. Dissolve the residue in ethyl acetate (100 mL) and wash with saturated sodium bicarbonate (100 mL). Extract the aqueous wash with ethyl acetate (100 mL). Combine the organic phase and the extract, wash with brine (100 mL), dry over anhydrous magnesium sulfate, pass through a short pad of silica gel and concentrate under vacuum to provide the cyclized compound (5.40 g) as an oil.

Step B

Scheme V, step E; Dissolve the above prepared cyclized compound (2.63 g, 10 mmol) in chloroform (100 mL) and trifluoroacetic acid (30 mL). Add triethylsilane (4.8 mL, 30 mmol) with stirring at room temperature. After about one week the reaction is concentrated under vacuum to provide the acid (3.21 g) shown below

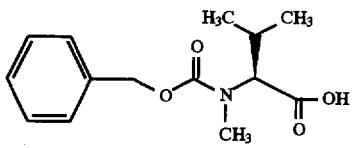

as a sticky oil.

The above acid can also be prepared following the procedure below. [see generally the procedure disclosed by Pitzele, B. S. et al., *J. Med. Chem.*, 37, 888–896, (1994).]

Step C

Scheme V, step C; Dissolve Cbz-Val-OH (10 g, 39.8 mmol) in THF (200 mL) and cool the solution to 0° C. Add sodium hydride (5 g, 120 mmol, 60% dispersion in oil) and stir for 20 minutes. Then add methyl iodide (3 mL, 48.2 mmol) and stir the reaction at 0° C. for 3 hours and at room temperature overnight. Slowly add water (100 mL) and wash the mixture with diethyl ether (50 mL). Acidify the aqueous layer with 6N HCl to approximately pH 3 and extract with ethyl acetate (4×100 mL). Combine the organic extracts, wash with 5% sodium thiosulfate (100 mL), brine (100 mL), dry over magnesium sulfate, pass through a short pad of silica gel and concentrate under vacuum to provide a mixture of starting material and desired acid (8.74 g). This mixture and additional Cbz-Val-OH (1.5 g) are dissolved in THF (200 mL). Cool the solution to 0° C. Add sodium hydride (5 g, 120 mmol, 60% dispersion in oil) and stir for 10 minutes. Then add methyl iodide (6 mL, 96.4 mmol) and heat the reaction at reflux overnight. After cooling to room temperature slowly add water (100 mL) and lithium hydroxide monohydrate (3 g) and stir for 3 hours. Wash the mixture with diethyl ether (100 mL). Acidify the aqueous layer with 6N HCl to approximately pH 3 and extract with ethyl acetate (3×100 mL). Combine the organic extracts, wash with 5% sodium thiosulfate (100 mL), brine (100 mL), dry over magnesium sulfate, pass through a short pad of silica gel and concentrate the filtrate under vacuum. The residue is dissolved in THF (100 mL) and water (100 mL), treated with lithium hydroxide monohydrate (3 g) and stirred at room temperature for 2 days. The reaction is then rinsed with diethyl ether (100 mL) and acidified with 6N HCl to approximately pH 3. Extract the aqueous layer with ethyl acetate (3×100 mL). Combine the organic extracts, wash with 5% sodium thiosulfate (100 mL), brine (100 mL), dry over magnesium sulfate, pass through a short pad of silica gel and concentrate the filtrate under vacuum to provide the acid (1.19 g).

Step D

Scheme III, step B; Dissolve HCl.Phe-OCH$_3$ (2.92 g, 11 mmol) in DMF (20 mL) and cool the solution to 0° C. Add triethylamine (1.7 mL, 12 mmol) and stir for 10 minutes. Then add the above formed acid (10 mmol, dissolved in 100 mL THF, the acid formed in either of the above alternative procedures may be used) followed by addition of HOBt (1.62 g, 12 mmol) and EDC (2.3 g, 12 mmol). Stir the reaction at 0° C. for 3 hours and then at room temperature overnight. Concentrate the reaction under vacuum and take up the residue in 1N HCL (100 mL) and extract with ethyl acetate (3×100 mL). Combine the organic extracts, rinse with saturated sodium bicarbonate (100 mL), brine (100 mL), dry over anhydrous magnesium sulfate, pass through a short pad of silica gel and concentrate under vacuum. Purify the residue by flash chromatography (silica gel, hexane/ethyl acetate, 95:5 then 9:1 then 8:2 then 6:4) to provide the coupled product (3.65 g, 86%).

Step E

Scheme III, step C; Dissolve the above prepared coupled product (3.30 g) in THF (100 mL) and water (50 mL). Add lithium hydroxide monohydrate (900 mg) and stir the reaction at room temperature overnight. Then wash the reaction with diethyl ether (100 mL) and acidify the aqueous layer with 6N HCl to approximately pH 2. Then extract the acidified aqueous layer with ethyl acetate (3×100 mL). Combine the organic extracts, dry over anhydrous magnesium sulfate, pass through a short pad of silica gel and concentrate the filtrate under vacuum to provide the acid (2.47 g, 77%) as an oil.

Step F

Scheme VI, step A; Combine the above prepared acid (2.40 g, 5.8 mmol) with paraformaldehyde (4.0 g) and p-toluenesulfonic acid monohydrate (200 mg) in 1,2-dichloroethane (200 mL) and heat at reflux for 6 hours with continuous removal of water via a Dean-Stark trap. After cooling, an additional amount of paraformaldehyde (2.0 g) is added and the reaction is heated at reflux overnight with continuous removal of water. After cooling, the reaction is concentrated under vacuum. The residue is dissolved in ethyl acetate (200 mL), washed with saturated sodium bicarbonate (100 mL), brine (100 mL), dried over anhydrous magnesium sulfate, passed through a short pad of silica gel and the filtrate is concentrated under vacuum. The residue is purified by flash chromatography (silica gel, hexane/ethyl acetate, 9:1 then 8:2) to provide the cyclized compound (980 mg, 40%) as a sticky oil.

Step G

Scheme VI, step B; Dissolve the above prepared cyclized compound (1.90 g, 4.48 mmol) in toluene (50 mL) and cool the solution to -78° C. With stirring, add diisobutylaluminum hydride (6 mL of a 1M solution in toluene, 6 mmol) and stir for one hour. Then add water (20 mL) and pour the mixture into 1N HCl (100 mL). Extract the mixture with ethyl acetate (3×100 mL). Combine the organic extracts, wash with brine (100 mL), dry over anhydrous magnesium sulfate, pass through a short pad of silica gel and concentrate the filtrate. Purify the residue by flash chromatography (silica gel, hexane/ethyl acetate, 8:2 then 6:4) to provide the final title compound (540 mg) as an oil; $[\alpha]^{20}_D$ –93.49 (c 1.00, CHCl$_3$).

EXAMPLE 5

Preparation of [4S-3[(R*),4α,5β]]-1-[[5-hydroxy-4-(phenylmethyl)-3-oxazolidinyl]carbonyl]-3-methylbutyl]methyl-carbamic acid, phenylmethyl ester.

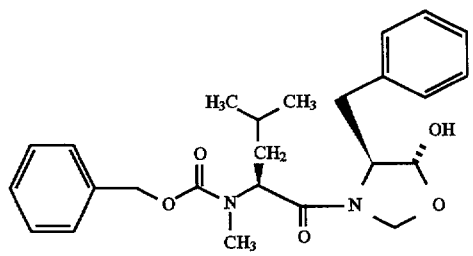

Step A

Scheme V, step C; Cbz-Leu (5.80 g, 21.9 mmol, obtained from Sigma Chemical Company) is dissolved in tetrahydrofuran (150 mL). Methyl iodide (11 mL, 176 mmol) is added and the solution is cooled to 0° C. Sodium hydride (3 g, 77 mmol, 60% dispersion in oil) is added to the solution, the reaction is stirred for 10 minutes and then allowed to warm to room temperature and stir for about 40 hours. 1N HCl (100 mL) is then added and the reaction is extracted with ethyl acetate (3×100 mL). The organic extracts are combined, washed with 5% sodium thiosulfate (100 mL), brine (100 mL), dried over anhydrous magnesium sulfate, passed through a short pad of silica gel and the filtrate concentrated under vacuum to provide the N-methylated product (7.36 g) as an oil.

Step B

Scheme III, step B; HCl.Phe-OCH₃ (4.75 g, 22 mmol) is dissolved in DMF (30 mL). The solution is cooled to 0° C. and triethylamine (6.2 mL, 44 mmol) is added. After 10 minutes, a solution of the above prepared N-methylated compound (7.36 g dissolved in 130 mL of DMF) is added to the solution, followed by addition of HOBT (2.97 g, 22 mmol) and EDC (4.2 g, 22 mmol). The reaction is stirred at 0° C. for 3 hours and then allowed to warm to room temperature overnight. The reaction is then concentrated under vacuum, the residue taken up in ethyl acetate (100 mL) and rinsed with 1N HCl (100 mL). The aqueous rinse is extracted with ethyl acetate (2×100 mL). The organic layer and the organic extracts are combined, rinsed with saturated sodium bicarbonate (100 mL), brine (100 mL), dried over anhydrous magnesium sulfate, passed through a short pad of silica gel and the filtrate concentrated under vacuum to provide the coupled product (10.26 g) as an oil.

Step C

Scheme III, step C; The above coupled product (10.26 g) is dissolved in THF (100 mL) and water (100 mL). The mixture is treated with lithium hydroxide-H₂O (1.0 g) and the reaction is stirred at room temperature for 2 hours. The reaction is then rinsed with diethyl ether (100 mL) and the aqueous is acidified with 6N HCl to approximately pH 2. The aqueous is then extracted with ethyl acetate (3×100 mL). The organic extracts are combined, rinsed with brine (100 mL), dried over anhydrous magnesium sulfate, passed through a short pad of silica gel and concentrated under vacuum to provide the acid (7.63 g) as a sticky oil.

Step D

Scheme VI, step A; The above prepared acid (7.50 g, 17.6 mmol) is combined with paraformaldehyde (6.0 g), p-toluenesulfonic acid.H₂O (700 mg) and 4A molecular sieves (19 g) in 1,2-dichloroethane (200 mL). The reaction is heated at reflux for 2.5 hours with removal of water via a Dean-Stark trap. The reaction is then cooled to room temperature and the solution is passed through a short pad of silica gel with ethyl acetate (400 mL). The filtrate is concentrated under vacuum and the residue is purified by flash chromatography (silica gel, hexane/ethyl acetate, 95:5 then 9:1 then 8:2) to provide the cyclized compound (5.19 g, 67%) as a sticky oil.

Steps E

Scheme VI, step B; The above cyclized compound (4.7 mmol) is reduced in a manner analogous to the procedure described in example 1, step using DIBAL (10 mmol) in toluene (60 mL) to provide the the title compound.

EXAMPLE 6

Preparation of [4S-[3(R*),4α,5β]]-[1-[[5-hydroxyl-4-(phenylmethyl)-3-oxazolidinyl]carbonyl]-3-methylbutyl]-carbamic acid, phenylmethyl ester.

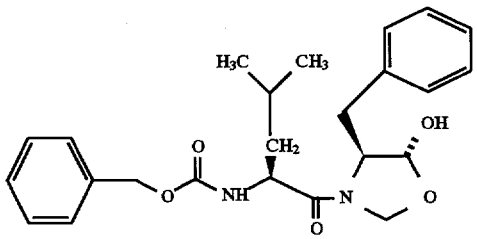

Step A

Scheme III, step B; HCl.Phe-O-tert-butyl (4.65 g, 18 mmol) is suspended in DMF (40 mL). The suspension is cooled to 0° C. and triethylamine (5.6 mL, 40 mmol) is added. After stirring for 10 minutes, THF (50 mL) is added, followed by addition of Cbz-Leu-OH (4.77 g, 18 mmol, in 100 mL THF), HOBt (2.6 g, 19 mmol) and EDC (3.63 g, 19 mmol). The reaction is stirred at 0° C. for 3 hours and then at room temperature overnight. The reaction is then concentrated under vacuum. The residue dissolved in 1N HCl (100 mL) and the aqueous extracted with ethyl acetate (4×100 mL). The organic extracts are combined, rinsed with saturated sodium carbonate (100 mL), brine (100 mL), dried over anhydrous magnesium sulfate, passed through a short pad of silica gel and the filtrate is concentrated under vacuum to provide the coupled product (9.93 g) as an oil.

Step B

Scheme III, step C; The above coupled product (9.93 g) is dissolved in methylene chloride (20 mL) and treated with trifluoroacetic acid (10 mL). The reaction is stirred overnight at room temperature and then concentrated under vacuum to provide the acid as a sticky oil.

Step C

Scheme VI, step A; The above prepared acid is dissolved in 1,2-dichloroethane (200 mL) and treated with paraformaldehyde (5 g), p-toluenesulfonic acid monohydrate (500 mg) and 4A molecular sieves (L9 g). The reaction is heated at reflux for approximately 18 hours with continuous removal of water via a Dean-Stark trap. The reaction is then cooled to room temperature and passed through a short pad of silica gel. The filtrate is concentrated under vacuum to provide an oil. The above pad of silica gel is rinsed with ethyl acetate (300 mL) which is combined with the above oil, rinsed with saturated sodium bicarbonate (100 mL), brine (100 mL), dried over anhydrous magnesium sulfate, passed through a short pad of silica gel and concentrated under vacuum. The residue is purified by flash chromatography (silica gel, hexane/ethyl acetate, 9:1 then 8:2 then 6:4) to provide the cyclized compound (1.04 g) as a foam.

Step D

Scheme VI, step B: The above cyclized compound (4.7 mmol) is reduced in a manner analogous to the procedure described in example 1, step using DIBAL (10 mmol) in toluene (60 mL) to provide the final title compound.

EXAMPLE 7

Preparation of [4S-[3(R*),4α,5β]]-N-[1-[[5-hydroxy-4-(phenylmethyl)-3-oxazolidinyl]carbonyl]-2-methylpropyl]-4-morpholinecarboxamide.

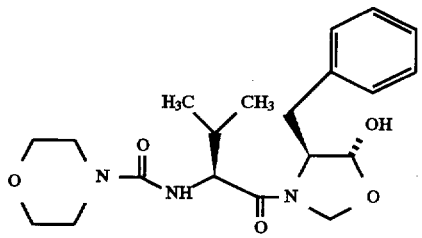

Step A

L-Valine (6.4 g, 54.6 mmol) is combined with sodium hydroxide (6.6 g, 160 mmol) in water (100 mL). The solution is cooled to 0° C. and a solution of 4-morpholinecarbonyl chloride (8 mL, 68.6 mmol) in diethyl ether (100 mL) is added dropwise with stirring. The reaction is stirred for 3 hours 0° C. and then at room temperature overnight. The layers are separated and the aqueous layer is acidified with 6N HCl to approximately pH 2. The acidified aqueous layer is then extracted with ethyl acetate (3×100 mL). The organic extracts are combined, dried over anhydrous magnesium sulfate, filtered and concentrated under vacuum to provide the coupled product (5.88 g).

Step B

Scheme III, step B; Dissolve HCl.Phe-OCH₃ (4.32 g, 20 mmol) in DMF (20 mL) and cool the solution to 0° C. Add triethylamine (6 mL) and stir for 10 minutes. Then add the above formed coupled product (4.56 g, 19.83 mmol, dissolved in 150 mL THF), followed by addition of HOBt (2.83 g, 21 mmol) and EDC (4.0 g, 21 mmol). Stir the reaction for 3 hours at 0° C. and then at room temperature overnight. Concentrate the reaction under vacuum and take up the residue in 1N HCl (100 mL) and extract with ethyl acetate (3×100 mL). Combine the organic extracts, rinse with saturated sodium bicarbonate (100 mL), brine (100 mL), dry over anhydrous magnesium sulfate, pass through a short pad of silica gel and concentrate under vacuum. Purify the residue by flash chromatography (silica gel, hexane/ethyl acetate) to provide the coupled product (5.60 g 72%) as a sticky oil.

Step C

Scheme III, step C; Dissolve the above prepared coupled product (5.6 g, 14.3 mmol) in THF (100 mL) and water (100 mL). Add lithium hydroxide monohydrate (670 mg, 16 mmol) and stir the reaction at room temperature for 2 hours. Then wash the reaction with diethyl ether (100 mL) and acidify the aqueous layer with 6N HCl to approximately pH 2. Then extract the acidified aqueous layer with ethyl acetate (3×100 mL). Combine the organic extracts, dry over anhydrous magnesium sulfate, pass through a short pad of silica gel and concentrate the filtrate under vacuum to provide the acid (4.58 g, 85%) as a foamy solid.

Step D

Scheme VI, step A; Combine the above prepared acid (5.8 mmol) with paraformaldehyde (4.0 g) and p-toluenesulfonic acid monohydrate (200 mg) in 1,2-dichloroethane (200 mL) and heat at reflux for 6 hours with continuous removal of water via a Dean-Stark trap. After cooling, the reaction is concentrated under vacuum. The residue is dissolved in ethyl acetate (200 mL), washed with saturated sodium bicarbonate (100 mL), brine (100 mL), dried over anhydrous magnesium sulfate, passed through a short pad of silica gel and the filtrate is concentrated under vacuum. The residue is purified by flash chromatography (silica gel, hexane/ethyl acetate) to provide the cyclized compound.

Step E

Scheme VI, step B; Dissolve the above prepared cyclized compound (4.48 mmol) in toluene (50 mL) and cool the solution to −78° C. With stirring, add diisobutylaluminum hydride (6 mL of a 1M solution in toluene, 6 mmol) and stir for one hour. Then add water (20 mL) and pour the mixture into 1N HCl (100 mL). Extract the mixture with ethyl acetate (3×100 mL). Combine the organic extracts, wash with brine (100 mL), dry over anhydrous magnesium sulfate, pass through a short pad of silica gel and concentrate the filtrate. Purify the residue by flash chromatography (silica gel, hexane/ethyl acetate) to provide the final title compound.

EXAMPLE 8

Preparation of [4S-[4α,5β]]-5-hydroxy-4-(phenylmethyl)-3-oxazolidinecarboxylic acid, phenylmethyl ester.

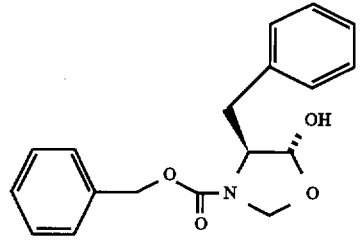

Step A

Scheme VI, step A; Combine Cbz-Phe-OH (2.5 g) with paraformaldehyde (5.0 g) and p-toluenesulfonic acid monohydrate (500 mg) in toluene (100 mL) and heat at reflux for 20 hours with continuous removal of water via a Dean-Stark trap. Cool the reaction to room temperature and concentrate under vacuum. Take up the residue in ethyl acetate (100 mL), rinse with saturated sodium bicarbonate (100 mL), brine (100 mL), dry over anhydrous magnesium sulfate, pass through a short pad of silica gel and concentrate under vacuum. Purify the residue by flash chromatography (silica gel, hexane/ethyl acetate, 9:1 then 8:2) followed by recrystallization from ethyl acetate/hexane with recovery of a second crop of crystals to provide the cyclized compound (2.10 g, 81%) as a white solid; $[\alpha]^{20}_D$+201.5 (c 1.00, CHCl₃); IR (KBr) 3032, 2966, 1792, 1683, 1433 cm$^{-1}$.

Anal. Calcd for $C_{18}H_{17}NO_4$: C, 69.44; H, 5.50; N, 4.50; Found C, 69.30; H, 5.51; N, 4.46.

Step B

Scheme VI, step B; The above cyclized compound (4.7 mmol) is reduced in a manner analogous to the procedure described in example 1, step using DIBAL (10 mmol) in toluene (60 mL) to provide the final title compound.

EXAMPLE 9

Preparation of [4S-[3(R*),4α,5β]]-[1-[[5-butyryloxy)-4-(phenylmethyl)-3-oxazolidinyl]carbonyl]-2-methylpropyl]-carbamic acid, phenylmethyl ester (MDL 103 821.

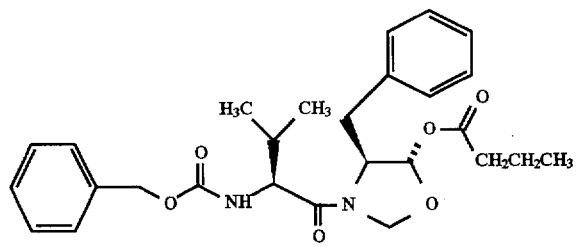

Scheme VII; Dissolve [4S-[3(R*),4α,5β]]-[1-[[5-hydroxy-4-(phenylmethyl)-3-oxazolidinyl]carbonyl]-2-methylpropyl]-carbamic acid, phenylmethyl ester (0.6 mmol, prepared in example 1) with triethylamine (0.3 mL) in methylene chloride (20 mL). Add butyryl chloride (4.2 mmol) to the solution at room temperature and stir the reaction overnight. Concentrate the reaction under vacuum and dissolve the residue in ethyl acetate (30 mL) and 1N HCl (30 mL). Separate the layers and extract the aqueous layer with ethyl acetate (3×30 mL). Combine the organic layer and organic extracts, dry over anhydrous magnesium sulfate, pass through a short pad of silica gel and concentrate the filtrate under vacuum. Purify the residue by flash chromatography (silica gel, hexane/ethyl acetate) to provide the title compound.

EXAMPLE 9A

Alternative Preparation of [b 4S-[3(R*),4α,5β]]-[1-[[5-(butyryloxy-4-(phenylmethyl)-3-oxazolidinyl]carbonyl]-2-methylpropyl]-carbamic acid, phenylmethyl ester (MDL 103,821).

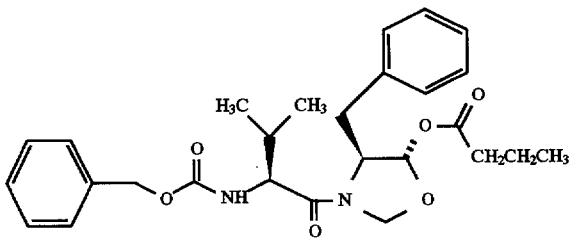

Scheme VII; Dissolve [4S-[3(R*),4α,5β]]-[1-[[5-hydroxy-4-(phenylmethyl)-3-oxazolidinyl]carbonyl]-2-methylpropyl]-carbamic acid, phenylmethyl ester (0.375 g), 0.909 mmol, prepared in example 1) in methylene chloride (3.6 mL). Add N-methylmorpholine (0.202 g, 2.00 mmol) and butyryl chloride (0.194 g, 1.82 mmol) and stir the reaction mixture overnight at room temperature in a sealed microvial. Transfer the reaction mixture to a separatory funnel along with 1N HCl (25 mL), saturated NaHCO₃ (1×25 mL) and dry over MgSO₄. Remove the solvent in vacuo and purify the residue by flash chromatography (silica gel, hexane/ethyl acetate (2:1), loading with methylene chloride) to give the title compound (0.328 g) as a viscous clear, colorless oil. $R_f$=0.56; $[α]^{20}_D$=56.4 (CHCl₃, C=0.700)

EXAMPLE 10

Preparation of [4S[3(R*),4α, 5β]]-[1-[[5-hydroxy-2,2-dimethyl-4-(phenylmethyl)-3-oxazolidinyl]carbonyl]-2-methylpropyl]-carbamic acid, phenylmethyl ester.

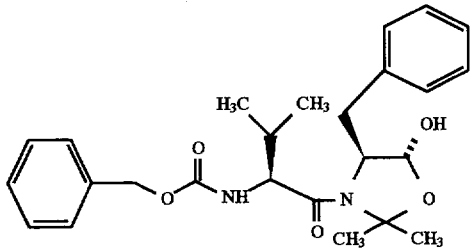

Step A

Scheme VI, step A; Combine Cbz-Val-Phe-OH (4.67 g, 11.7 mmol, obtained from Sigma Chemical Company, St. Louis, Mo.) with acetone (5 g) and p-toluenesulfonic acid monohydrate (500 mg, 2.6 mmol) in benzene (120 mL). Heat the reaction at reflux for approximately 23 hours with continuous removal of water via a Dean-Stark trap. Cool the reaction to room temperature and concentrated under vacuum. Dissolve the residue in ethyl acetate (100 mL) and rinsed with saturated aqueous sodium bicarbonate (60 mL). Extract the aqueous rinse with ethyl acetate (2×50 mL). Combine the organic layer and organic extracts, dry over anhydrous magnesium sulfate, pass through a short pad of silica gel and concentrate the filtrate under vacuum. The residue is then purified by flash chromatography to provide the cyclized compound.

Step B

Scheme VI, step B; The above cyclized compound (4.7 mmol) is reduced in a manner analogous to the procedure described in example 1, step using DIBAL (10 mmol) in toluene (60 mL) to provide the final title compound.

EXAMPLE 11

Preparation of [4S-[3(R*),4α,5β]]-[1-[[5-(acetyloxy)-2,2-dimethyl-4-(phenylmethyl)-3-oxazolidinyl]carbonyl]-2-methyl-carbamic acid, phenylmethyl ester.

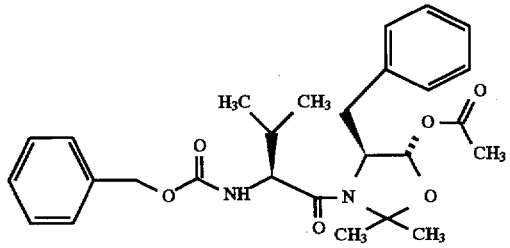

Scheme VII; [4S-[3(R*),4α,5β]]-[1-[[5-hydroxy-2,2-dimethyl-4-(phenylmethyl)-3-oxazolidinyl]carbonyl]-2-methylpropyl]-carbamic acid, phenylmethyl ester (0.6 mmol, prepared in example 10) and triethylamine (0.3 mL) are dissolved in methylene chloride (20 mL). Acetyl chloride (0.3 mL, 4.2 mmol) is then added to the solution at room temperature and the reaction is stirred overnight. The reaction is then concentrated under vacuum and the residue is dissolved in ethyl acetate (30 mL) and 1N HCl (30 mL). The layers are separated and the aqueous layer is extracted with ethyl acetate (3×30 mL). The organic layer and organic extracts are combined, dried over anhydrous magnesium sulfate, passed through a short pad of silica gel and the filtrate is concentrated under vacuum. The residue is purified by flash chromatography (hexane/ethyl acetate, 80:20, silica gel) to provide the title compound.

EXAMPLE 12

Preparation of [2R-[2α,3,(S*),4β,5α]]-[1-[[5-hydroxy-2-methyl-4-(phenylmethyl)-3-oxazolidinyl]carbonyl]-2-methylpropyl]-carbamic acid, phenylmethyl ester, (C); and [2S-[2α,3,(R*),4α,5β]]-[1-[[5-hydroxy-2-methyl-4-(phenylmethyl)-3-oxazolidinyl]carbonyl]-2-methylpropyl]-carbamic acid, phenylmethyl ester, (D).

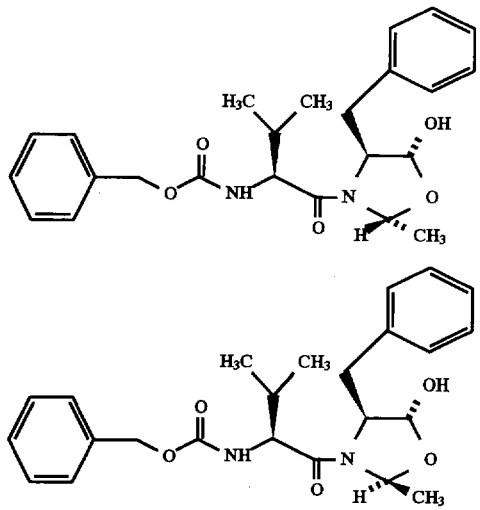

Step A

Scheme VI, step A; Combine Cbz-Val-Phe-OH (4.67 g, 11.7 mmol, obtained from Sigma Chemical Company, St. Louis, Mo.) with acetaldehyde (5 g) and p-toluenesulfonic acid monohydrate (500 mg, 2.6 mmol) in benzene (120 mL). Heat the reaction at reflux for approximately 23 hours with continuous removal of water via a Dean-Stark trap. Cool the reaction to room temperature and concentrated under vacuum. Dissolve the residue in ethyl acetate (100 mL) and rinse with saturated aqueous sodium bicarbonate (60 mL). Extract the aqueous rinse with ethyl acetate (2×50 mL). Combine the organic layer and organic extracts, dry over anhydrous magnesium sulfate, pass through a short pad of silica gel and concentrate the filtrate under vacuum to provide the cyclized compound as a mixture of isomers A and B.

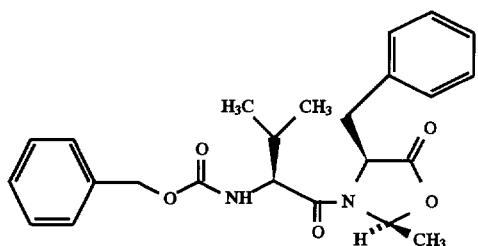

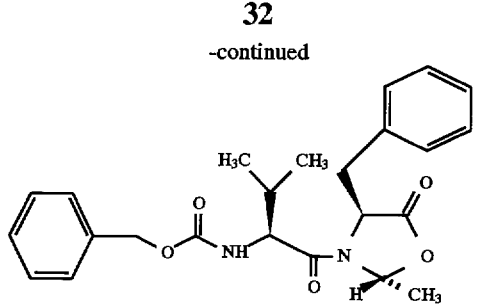

The above isomers can then be individually isolated from the mixture by flash chromatography. Alternatively, the mixture can be carried on to the reduction step and the isomers then separated after reduction with DIBAL.

Step B

Scheme VI, step B; Either of the above cyclized compounds, A or B (4.7 mmol) or the mixture of compounds A and B are reduced in a manner analogous to the procedure described in example 1, step using DIBAL (10 mmol) in toluene (60 mL) to provide the final title compounds C and D.

EXAMPLE 13

Preparation of [2R-[2α,3,(S*),4β,5α]]-[1-[[5-hydroxy-2-(phenylmethyl)-4-(phenylmethyl)-3-oxazolidinyl]carbonyl]-2-methylpropyl]-carbamic acid, phenylmethyl ester, (C); and [2S-[2α,3,(R*),4α,5β]]-[1-[[5-hydroxy-2-(phenylmethyl)-4-(phenylmethyl)-3-oxazolidinyl]carbonyl]-2-methylpropyl]-carbamic acid, phenylmethyl ester, (D).

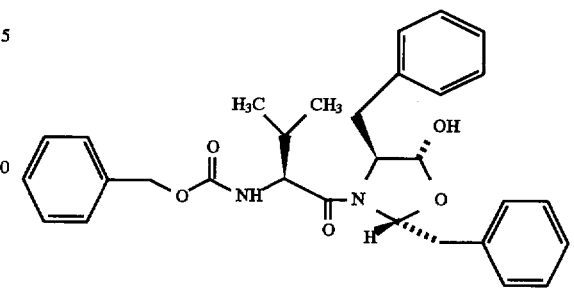

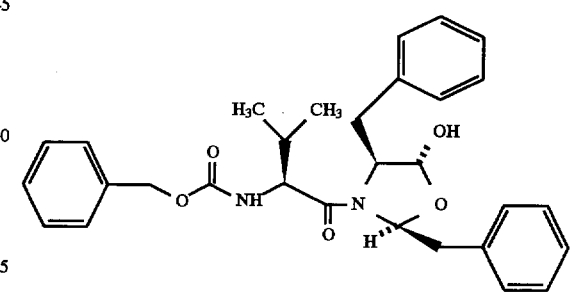

Step A

Scheme VI, step A; Combine Cbz-VaL-Phe-OH (4.67 g 11.7 mmol, obtained from Sigma Chemical Company, St. Louis, Mo. 63178) with phenylacetaldehyde (5 g) and p-toluenesulfonic acid monohydrate (500 mg, 2.6 mmol) in benzene (120 mL). Beat the reaction at reflux for approximately 23 hours with continuous removal a Dean-Stark trap. Cool the reaction to room temperature and concentrated under vacuum. Dissolve the residue ethyl acetate (100 mL) and rinse with saturated aqueous sodium bicarbonate (60 mL). Extract the aqueous rinse with ethyl acetate (2×50 mL).

Combine the organic layer organic extracts, dry over anhydrous magnesium sulfate, pass through a short pad of silica gel and concentrate the filtrate under vacuum to provide the cyclized compound as a mixture of isomers A and B.

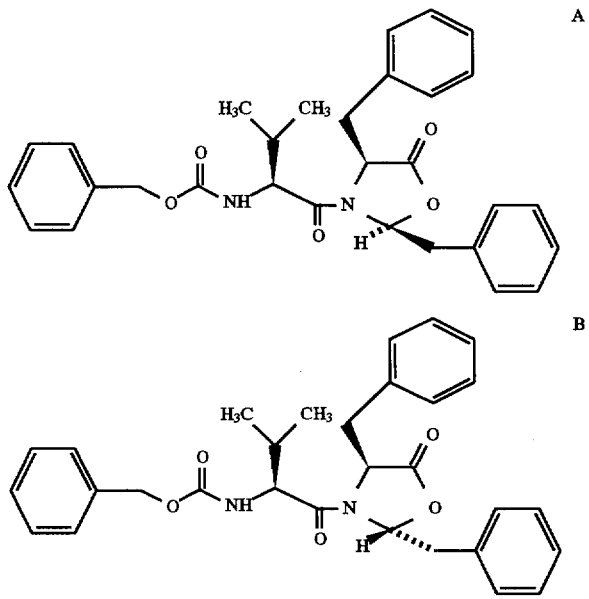

The above isomers can then be isolated from the mixture by flash chromatography. Alternatively, the mixture can be carried on to the reduction step and the isomers then separated after reduction with DIBAL.

Step B

Scheme VI, step B; Either of the above cyclized compounds, A or B (4.7 mmol) or the mixture of compounds A and B are reduced in a manner analogous to the procedure described in example 1, step B using DIBAL (10 mmol) in toluene (60 mL) to provide the final title compounds C and D.

EXAMPLE 14

Preparation of [4S-[3(R*),4α,5β]]-[1-[[5-hydroxy-4-[(4-hydroxyphenyl)methyl]-3-oxazolidinyl]carbonyl]-2-methylpropyl]-carbamic acid, phenylmethyl ester.

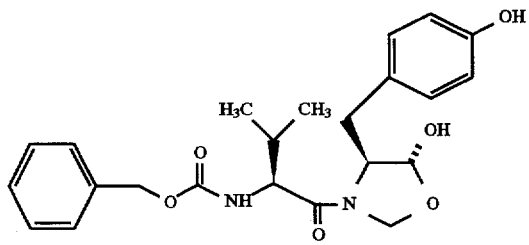

Step A

Scheme III, step B; HCl.Tyr-O-tert-butyl (18 mmol) is suspended in DMF (40 mL). The suspension is cooled to 0° C. and triethylamine (5.6 mL, 40 mmol) is added. After stirring for 10 minutes, THF (50 mL) is added, followed by addition of Cbz-Val-OH (18 mmol, in 100 mL THF), HOBt (2.6 g, 19 mmol) and EDC (3.63 g, 19 mmol). The reaction is stirred at 0° C. for 3 hours and then at room temperature overnight. The reaction is then concentrated under vacuum. The residue is dissolved in 1N HCl (100 mL) and the aqueous extracted with ethyl acetate (4×100 mL). The organic extracts are combined, rinsed with saturated sodium carbonate (100 mL), brine (100 mL), dried over anhydrous magnesium sulfate, filtered and concentrated under vacuum to provide the coupled product.

Step B

Scheme III, step C; The above coupled product is dissolved in methylene chloride (20 mL) and treated with trifluoroacetic acid (10 mL). The reaction is stirred overnight at room temperature and then concentrated under vacuum to provide the acid as a sticky oil.

Step C

Scheme VI, step A; The above prepared acid (5.8 mmol) is cyclized in a manner analogous to the procedure described in example 1, step A with paraformaldehyde (4.0 g), p-toluenesulfonic acid monohydrate (200 mg) and 1,2dichloroethane (200 mL), to provide the cyclized compound after flash chromatography (silica gel, hexane/ethyl acetate).

Step D

Scheme VI, step B; The above cyclized compound (4.7 mmol) is reduced in a manner analogous to the procedure described in example 1, step B using DIBAL (10 mmol) in toluene (60 mL) to provide the final title compound.

EXAMPLE 15

Preparation of [4S-[3(R*),4α,5β]]-[1-[[5-hydroxy-4-[4-methoxyphenyl)methyl]-3-oxazolidinyl]carbonyl]-2-methylpropyl]-carbamic acid, phenylmethyl ester.

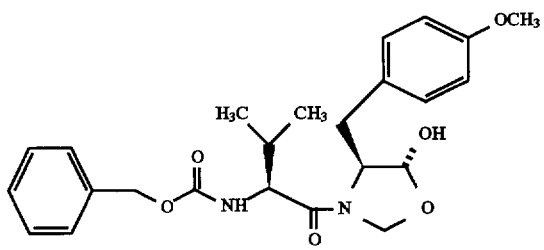

Step A

Scheme III, step B; To a solution of N-Benzyloxycarbonyl-L-valine anhydride (0.339 g, 0.7 mmol) in anhydrous dichloromethane (15 ml) is added O-methyl-L-tyrosine, benzyl ester, toluene-4-sulfonate (0.330 g, 0.7 mmol) and N-methyl morpholine (0.081 g, 0.8 mmol). The reaction is stirred at room temperature overnight. The reaction is concentrated under vacuum and the residue is purified by flash chromatography (silica gel: 2:8 ethyl acetate/cyclohexane) to provide the coupled compound.

Step B

Scheme III, step C; Dissolve the above prepared coupled product (14.3 mmol) in THF (100 mL) and water (100 mL). Add lithium hydroxide monohydrate (670 mg, 16 mmol) and stir the reaction at room temperature for 2 hours. Then wash the reaction with diethyl ether (100 mL) and acidify the aqueous layer with 6N HCl to approximately pH 2. Extract the acidified aqueous layer with ethyl acetate (3×100 mL). Combine the organic extracts, dry over anhydrous magnesium sulfate, filter and concentrate the filtrate under vacuum to provide the acid.

Step C

Scheme VI, step A; The above prepared acid (5.8 mmol) is cyclized in a manner analogous to the procedure described in example 1, step A with paraformaldehyde (4.0 g), p-toluenesulfonic acid monohydrate (200 mg) and 1,2-dichloroethane (200 mL), to provide the cyclized compound after flash chromatography (silica gel, hexane/ethyl acetate).

Step D

Scheme VI, step B; The above cyclized compound (4.7 mmol) is reduced in a manner analogous to the procedure described in example 1, step B using DIBAL (10 mmol) in toluene (60 mL) to provide the final title compound.

EXAMPLE 16

Preparation of [4S-[3(R*),4α,5β]]-[1-[[5-hydroxy-4-[(4nitrophenyl)methyl]-3-oxazolidinyl)carbonyl]-2-methylpropyl]-carbamic acid, phenylmethyl ester.

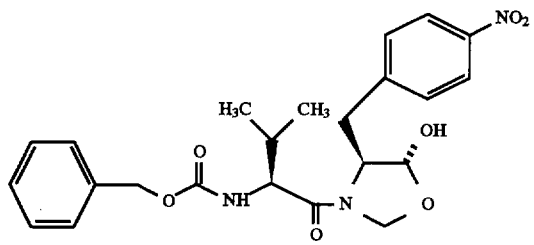

Step A

Scheme III, step B; To a solution of L-valine anhydride (4.80 g, 10 mmol) in anhydrous dichloromethane (50 ml) is added 4-nitro-L-phenylalanine methyl ester (2.24 g, 10 mmol). The mixture is stirred at room temperature overnight. The reaction is concentrated under vacuum and the residue is purified by flash chromatography (silica gel: 4:6 ethyl acetate/cyclohexane) to provide N-Benzyloxycarbonyl-L-valyl-4-nitro-L-phenylalanine methyl ester. $R_f$=0.32 (ethyl acetate/cyclohexane 1:1).

Step B

Scheme III, step C; Dissolve N-Benzyloxycarbonyl-L-valyl-4-nitro-L-phenylalanine methyl ester (14.3 mmol, prepared above) in THF (100 mL) and water (100 mL). Add lithium hydroxide monohydrate (670 mg, 16 mmol) and stir the reaction at room temperature for 2 hours. Then wash the reaction with diethyl ether (100 mL) and acidify the aqueous layer with 6N HCl to approximately pH 2. Extract the acidified aqueous layer with ethyl acetate (3×100 mL). Combine the organic extracts, dry over anhydrous magnesium sulfate, filter and concentrate the filtrate under vacuum to provide the acid.

Step C

Scheme VI, step A; The above prepared acid (5.8 mmol) is cyclized in a manner analogous to the procedure described in example 1, step A with paraformaldehyde (4.0 g), p-toluenesulfonic acid monohydrate (200 mg) and 1,2-dichloroethane (200 mL), to provide the cyclized compound after flash chromatography (silica gel, hexane/ethyl acetate).

Step D

Scheme VI, step B; The above cyclized compound (4.7 mmol) is reduced in a manner analogous to the procedure described in example 1, step B using DIBAL (10 mmol) in toluene (60 mL) to provide the final title compound.

EXAMPLE 17

Preparation of [4S-[3(R*),4α,5β]]-[1-[[4-[(4-aminophenyl)methyl]-5-hydroxy-3-oxazolidinyl] carbonyl]-2-methylpropyl]-carbamic acid, phenylmethyl ester.

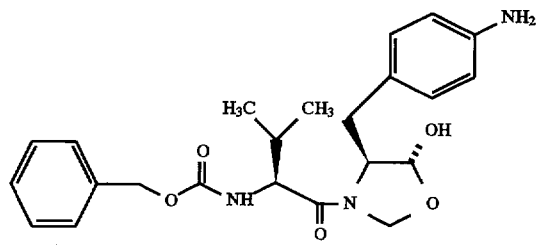

Step A

A solution of N-benzyloxycarbonyl-L-valyl-4-nitro-L-phenylalanine methyl ester (0.91 g, 2 mmol, prepared in example 15) and Tin (II) chloride dihydrate (1.56 g, mmol) in absolute ethanol (50 ml) and N,N-dimethylformamide (5 ml) is heated under reflux for 4 hours. The mixture is cooled, diluted with water, neutralized with sodium hydrogenocarbonate and extracted with ethyl acetate (3×50 ml). The organic extracts are combined, dried over anhydrous magnesium sulfate, filtered and concentrated under vacuum to provide the amine compound.

Step B

Scheme III, step C; The above prepared amino compound (14.3 mmol) is deprotected in manner analogous to the procedure described in example 16, step B with lithium hydroxide monohydrate (16 mmol) in water (100 mL) and THF (100 mL) to provide the acid.

Step C

Scheme VI, step A; The above prepared acid (5.8 mmol) is cyclized in a manner analogous to the procedure described in example 1, step A with paraformaldehyde (4.0 g), p-toluenesulfonic acid monohydrate (200 mg) and 1,2-dichloroethane (200 mL), to provide the cyclized compound after flash chromatography (silica gel, hexane/ethyl acetate).

Step D

Scheme VI, step B; The above cyclized compound (4.7 mmol) is reduced in a manner analogous to the procedure described in example 1, step B using DIBAL (10 mmol) in toluene (60 mL) to provide the final title compound.

EXAMPLE 18

Preparation of [4S-[3[R*(1R*,2R*)],4α,5β]]-[1-[[ [1-[[5-hydroxy -4-(phenylmethyl)-3-oxazolidinyl] carbonyl]-2-methylpropyl]amino]carbonyl]-2-methylbutyl-carbamic acid, phenylmethyl ester.

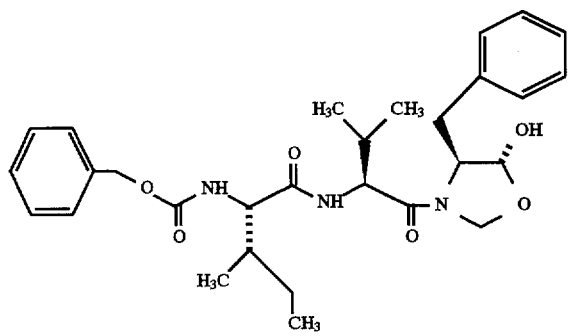

Step A

Scheme III, step A; HCl.Phe-OCH₃ (4.75 g, 22 mmol) is dissolved in DMF (30 mL). The solution is cooled to 0° C. and triethylamine (6.2 mL, 44 mmol) is added. After 10 minutes, a solution of N-t-butoxycarbonyl-Val (22 mmol dissolved in 130 mL of DMF) is added to the solution, followed by addition of HOBT (2.97 g, 22 mmol) and EDC (4.2 g, 22 mmol). The reaction is stirred at 0° C. for 3 hours and then allowed to warm to room temperature overnight. The reaction is then concentrated under vacuum, the residue taken up in ethyl acetate (100 mL) and rinsed with 1N HCl (100 mL). The aqueous rinse is extracted with ethyl acetate (2×100 mL). The organic layer and the organic extracts are combined, rinsed with saturated sodium bicarbonate (100 mL), brine (100 mL), dried over anhydrous magnesium sulfate, passed through a short pad of silica gel and the filtrate concentrated under vacuum to provide the coupled product.

Step B

Scheme IV, step B1; The above coupled product is dissolved in methylene chloride (20 mL) and treated with trifluoroacetic acid (10 mL). The reaction is stirred overnight at room temperature and then concentrated under vacuum to provide deprotected amine.

Step C

Scheme IV, step B2; The above prepared deprotected amine (22 mmol) is dissolved in DMF (30 mL). The solution is cooled to 0° C. and triethylamine (6.2 mL, 44 mmol) is added. After 10 minutes, a solution of Cbz-Ile (22 mmol dissolved in 130 mL of DMF) is added to the solution, followed by addition of HOBT (2.97 g, 22 mmol) and EDC (4.2 g, 22 mmol). The reaction is stirred at 0° C. for 3 hours and then allowed to warm to room temperature overnight. The reaction is then concentrated under vacuum, the residue taken up in ethyl acetate (100 mL) and rinsed with 1N HCl (100 mL). The aqueous rinse is extracted with ethyl acetate (2×100 mL). The organic layer and the organic extracts are combined, rinsed with saturated sodium bicarbonate (100 mL), brine (100 mL), dried over anhydrous magnesium sulfate, passed through a short pad of silica gel and the filtrate concentrated under vacuum to provide the coupled product.

Step D

Scheme IV, step C; The above prepared coupled product (14.3 mmol) is deprotected in manner analogous to the procedure described in example 16, step B with lithium hydroxide monohydrate (16 mmol) in water (100 mL) and THF (100 mL) to provide the acid.

Step E

Scheme VI, step A; The above prepared acid (5.8 mmol) is cyclized in a manner analogous to that described in example 1, step A with paraformaldehyde (4.0 g), p-toluenesulfonic acid monohydrate (200 mg) and 1,2-dichloroethane (200 mL), to provide the cyclized compound after flash chromatography (silica gel, hexane/ethyl acetate).

Step F

Scheme VI, step B; The above cyclized compound (4.7 mmol) is reduced in a manner analogous to that described in example 1, step B using DIBAL (10 mmol) in toluene (60 mL) to provide the final title compound.

EXAMPLE 19

Preparation of [4S-[3[R*(1R*,2R*)],4α,5β]]-[1-[[ [1-[[5-(acetyloxy)-4-(phenylmethyl)-3-oxazolidinyl] carbonyl]-2-methylpropyl]amino]carbonyl]-2-methylbutyl-carbamic acid, phenylmethyl ester.

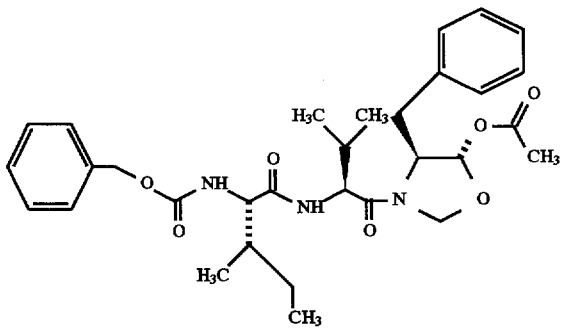

Scheme VII; [4S-[3[R*(1R*,2R*)],4α,5β]]-[1-[[[1-[[5-hydroxy-4-(phenylmethyl)-3-oxazolidinyl]carbonyl]-2-methylpropyl]amino]carbonyl]-2-methylbutyl-carbamic acid, phenylmethyl ester (0.6 mmol, prepared in example 18) and triethylamine (0.3 mL) are dissolved in methylene chloride (20 mL). Acetyl chloride (0.3 mL, 4.2 mmol) is then added to the solution at room temperature and the reaction is stirred overnight. The reaction is then concentrated under vacuum and the residue is dissolved in ethyl acetate (30 mL) and 1N HCl (30 mL). The layers are separated and the aqueous layer is extracted with ethyl acetate (3×30 mL). The organic layer and organic extracts are combined, dried over anhydrous magnesium sulfate, passed through a short pad of silica gel and the filtrate is concentrated under vacuum. The residue is purified by flash chromatography (hexane/ethyl acetate, 80:20, silica gel) to provide the title compound.

EXAMPLE 20

Preparation of [4S-[3[R*(!R*)],4α,5β]]-1-[[[1-[[5-hydroxy-4-(phenylmethyl)-3-oxazolidinyl]carbonyl]-2-methylpropyl]amino]carbonyl]-2-methylpropyl-carbamic acid, phenylmethyl ester.

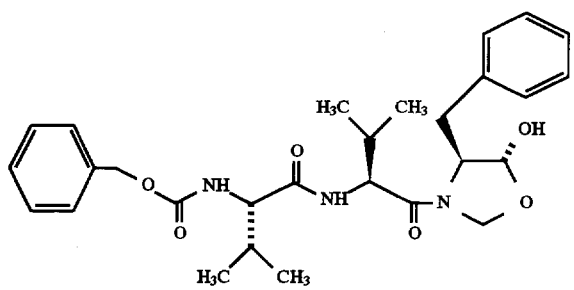

Step A

Scheme IV, step B2; The deprotected amine prepared in example 17, step B (22 mmol) is dissolved in DMF (30 mL). The solution is cooled to 0° C. and triethylamine (6.2 mL, 44 mmol) is added. After 10 minutes, a solution of Cbz-Val (22 mmol dissolved in 130 mL of DMF) is added to the solution, followed by addition of HOBT (2.97 g, 22 mmol) and EDC (4.2 g, 22 mmol). The reaction is stirred at 0° C. for 3 hours and then allowed to warm to room temperature overnight. The reaction is then concentrated under vacuum, the residue taken up in ethyl acetate (100 mL) and rinsed with 1N HCl (100 mL). The aqueous rinse is extracted with ethyl acetate (2×100 mL). The organic layer and the organic extracts are combined, rinsed with saturated sodium bicarbonate (100 mL), brine (100 mL), dried over anhydrous magnesium sulfate, passed through a short pad of silica gel and the filtrate concentrated under vacuum to provide the coupled product.

Step B

Scheme IV, step C; The above prepared coupled product (14.3 mmol) is deprotected in a manner analogous to the procedure described in example 16, step B with lithium hydroxide monohydrate (16 mmol) in water (100 mL) and THF (100 mL) to provide the acid.

Step C

Scheme VI, step A; The above prepared acid (5.8 mmol) is cyclized in a manner analogous to that described in example 1, step A with paraformaldehyde (4.0 g), p-toluenesulfonic acid monohydrate (200 mg) and 1,2-dichloroethane (200 mL), to provide the cyclized compound after flash chromatography (silica gel, hexane/ethyl acetate).

Step D

Scheme VI, step B; The above cyclized compound (4.7 mmol) is reduced in a manner analogous to the procedure described in example 1, step B using DIBAL (10 mmol) in toluene (60 mL) to provide the final title compound.

EXAMPLE 21

Preparation of [4S-[3[R*(!R*)],4α,5β]]-1-[[[-1-[[5-(acetyloxy)-4-(phenylmethyl)-3-oxazolidinyl]carbonyl]-2-methylpropyl]amino]carbonyl]-2-methylpropyl-carbamic acid, phenylmethyl ester.

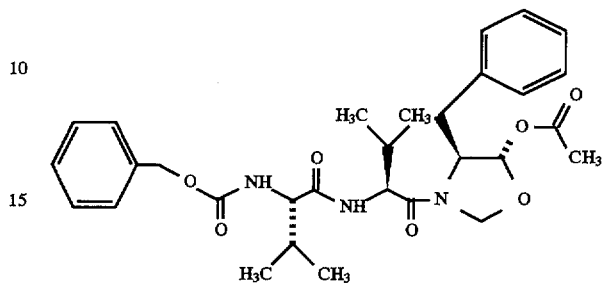

Scheme VII; The title compound of example 20 (0.6 mmol) is O-acylated in a manner analogous to the procedure described in example 19 with acetyl chloride (4.2 mmol) and triethylamine (0.3 mL) in methylene chloride (20 mL) to provide the title compound.

EXAMPLE 22

Preparation of

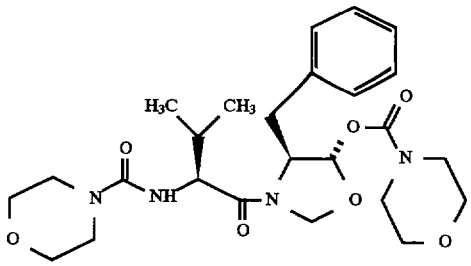

Scheme VII; The title compound prepared in example 7 (0.59 mmol) is O-acylated in a manner analogous to the procedure described in example 3 with 4-morpholinecarbonyl chloride (0.86 mmol), DMAP (10 mg) and triethylamine (1.2 mmol) in methylene chloride (30 mL) to provide the title compound.

EXAMPLE 23

Preparation of [4S-[3(R*),4α,5β]]-N-[1-[[5-hydroxy-4-(phenylmethyl)-3-oxazolidinyl]carbonyl]-2-methylpropyl]methyl-4-morpholinecarboxamide.

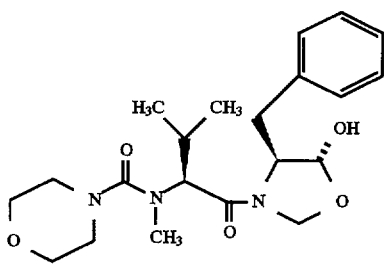

41

Step A

Scheme V, step D; The compound of the structure below

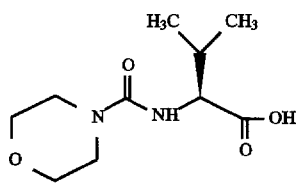

(11.7 mmol, prepared in example 7, step A) is cyclized in a manner analogous to the procedure described in example 1, step A with paraformaldehyde (5 g) and p-toluenesulfonic acid monohydrate (500 mg) in benzene (120 mL) to provide the cyclized compound.

Step B

Scheme V, step E; The above prepared cyclized compound (10 mmol) is reduced in a manner analogous to the procedure described in example 4, step B with trifluoroacetic acid (30 mL) and triethylsilane (30 mmol) in chloroform (100 mL) to provide the N-methylated compound.

Step C

Scheme III, step B; The above prepared N-methylated compound (10 mmol) is coupled with HCl.Phe-OCH₃ (11 mmol) in a manner analogous to the procedure described in example 4, step D using triethylamine (12 mmol), HOBt (12 mmol) and EDC (12 mmol) in DMF (20 mL) and THF (100 mL) to provide the coupled compound.

Step D

Scheme III, step C; The above prepared coupled compound (14.3 mmol) is deprotected in a manner analogous to the procedure described in example 7, step C with lithium hydroxide monohydrate (16 mmol) in water (100 mL) and THF (100 mL) to provide the acid.

Step E

Scheme VI, step A; The above acid (5.8 mmol) is cyclized in a manner analogous to the procedure described in example 4, step F with paraformaldehyde (4.0 g) and p-toluenesulfonic acid monohydrate in 1,2-dichloroethane (200 mL) to provide the cyclized compound.

Step F

Scheme VII, step C; The above prepare cyclized compound (4.48 mmol) is reduced in a manner analogous to the procedure described in example 4, step G with DIBAL (6 mmol) in toluene (50 mL) to provide the title compound.

EXAMPLE 24

Preparation of

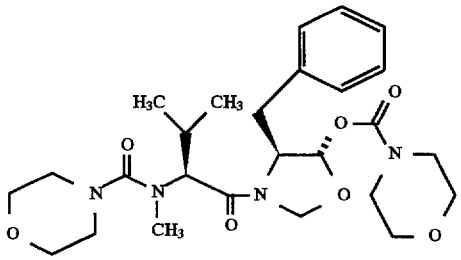

Scheme VII; The title compound prepared in example 23 (0.59 mmol) is O-acylated in a manner analogous to the procedure described in example 3 with 4-morpholinecarbonyl chloride (0.86 mmol), DMAP (10 mg) and triethylamine (1.2 mmol) to provide the title compound.

42

EXAMPLE 25

Preparation of [4S-[3(R*),4α,5β)]]-[1-[[4-[(4-chlorophenyl)methyl]-5-hydroxy-3-oxazolidinyl]carbonyl]-2-methylpropyl]-carbamic acid, phenylmethyl ester.

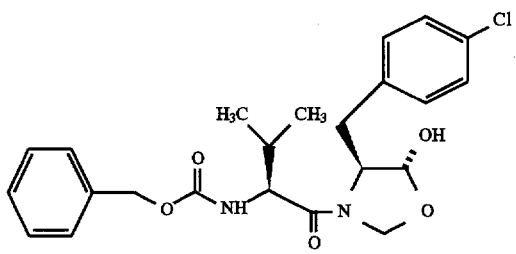

Step A

N-BOC-p-chloro-L-Phe (20 mmol, commercially available from Sigma Chemical Company, St. Louis, Mo. 63178) is dissolved in diethyl ether (400 mL), cooled to 0° C. and treated with a slight excess of diazomethane (faint yellow color persists). Several drops of dilute acetic acid are added to quench the excess diazomethane. The reaction is then rinsed with brine (200 mL), dried over anhydrous magnesium sulfate, filtered and concentrated to provide the methyl ester (N-BOC-p-chloro-L-Phe-OCH₃).

Step B

Scheme IV, step B1; The above prepared methyl ester is deprotected in a manner analogous to the procedure described in example 18, step B with trifluoroacetic acid (10 mL) in methylene chloride (20 mL) to provide the deprotected compound, (p-chloro-L-Phe-OCH₃).

Step C

Scheme IV, step B2; The above prepared deprotected compound (22 mmol) is coupled with CBz-Val (22 mmol dissolved in 130 mL DMF) in a manner analogous to the procedure described in example 18, step C with triethylamine (44 mmol), HOBt (22 mmol) and EDC (22 mmol) to provide the coupled compound.

Step D

Scheme IV, step C; The above prepared coupled compound (14.3 mmol) is deprotected in a manner analogous to the procedure described in example 7, step C with lithium hydroxide monohydrate (16 mmol) in water (100 mL) and THF (100 mL) to provide the acid.

Step E

Scheme VI, step A; The above prepared acid (5.8 mmol) is cyclized in a manner analogous to the procedure described in example 1, step A with paraformaldehyde (4.0 g) and p-toluenesulfonic acid monohydrate (200 mg) in 1,2-dichloroethane to provide the cyclized compound.

Step F

Scheme VI, step B; The above prepared cyclized compound (4.7 mmol) is reduced in a manner analogous to the procedure described in example 1, step B with DIBAL (10 mmol) in toluene (60 mL) to provide the final title compound.

EXAMPLE 26

Preparation of [4S-[3-(R*),4α,5β]]-3-[3-methyl-1-oxo-2-[[(phenylmethoxy)carbonyl]amino]butyl]-4-[(4-chlorophenyl)methyl]-5-oxazolidinyl ester, 4-morpholinecarboxylic acid.

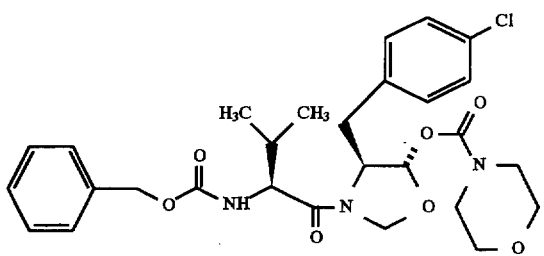

Scheme VII; The title compound prepared in example 25 (0.59 mmol) is O-acylated in a manner analogous to the procedure described in example 3 with 4-morpholinecarbonyl chloride (0.86 mmol), DMAP (10 mg) and triethylamine (1.2 mmol) in methylene chloride (30 mL) to provide the title compound.

EXAMPLE 27

Preparation of [4S-[3(R*),4α,5β]]-[1-[[5-hydroxy-4-(phenylmethyl)-3-oxazolidinyl]carbonyl]-ethyl]-carbamic acid, phenylmethyl ester.

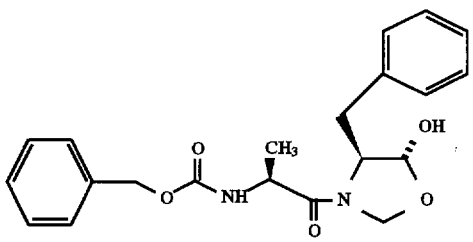

Step A

Scheme VI, step A; N-CBz-Ala-Phe-OH (11.7 mmol, available from Sigma Chemical Company, St. Louis, Mo. 63178) is cyclized in a manner analogous to the procedure described in example 1, step A with paraformaldehyde (5 g) and p-toluenesulfonic acid monohydrate (500 mg) in benzene to provide the cyclized compound. Step B Scheme VI, Step B; The above prepared cyclized compound (4.7 mmol) is reduced in a manner analogous to the procedure described in example 1, step B with DIBAL (10 mmol) in toluene (50 mL) to provide the title compound.

EXAMPLE 28

Preparation of [4S-[3(R*),4α,5β]]-3-[1-oxo-2-[[(phenylmethoxy)carbonyl]amino]propyl]-4-(phenylmethyl)-5-oxazolidinyl ester, 4-morpholinecarboxylic acid.

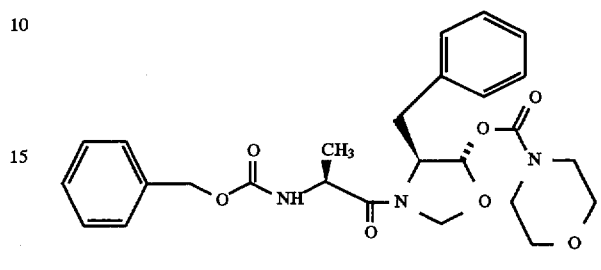

Scheme VII; The title compound prepared in example 27 (0.59 mmol) is O-acylated in a manner analogous to the procedure described in example 3 with 4-morpholinecarbonyl chloride (0.86 mmol), DMAP (10 mg) and triethylamine mmol) in methylene chloride (30 mL) to provide

EXAMPLE 29

Preparation of [4S-[3(R*),4α,5β]]-[1-[[5-hydroxy-4-(phenylmethyl)-3-oxazolidinyl]carbonyl]-2-methylbutyl]-carbamic acid, phenylmethyl ester.

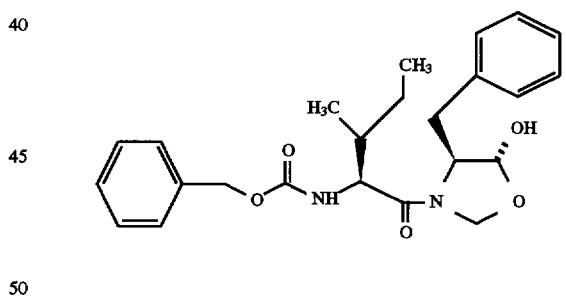

Step A

Scheme VI, Step A; N-CBz-Ile-Phe-OH (11.7 mmol, available from Sigma Chemical Company, St. Louis, Mo. 63178) is cyclized in a manner analogous to the procedure described in example 1, step A with paraformaldehyde (5 g) and p-toluenesulfonic acid monohydrate (500 mg) in benzene to provide the cyclized compound.

Step B

Scheme VI, Step B; The above prepared cyclized compound (4.7 mmol) is reduced in a manner analogous to the procedure described in example 1, step B with DIBAL (10 mmol) in toluene (50 mL) to provide the title compound.

EXAMPLE 30

Preparation of [4S-[3(R*),4α,5β]]-3-[3-methyl-1-oxo-2-[[(phenylmethoxy)carbonyl]amino pentyl]-4-(phenylmethyl)-5-oxazolidinyl ester, 4-morpholinecarboxylic acid.

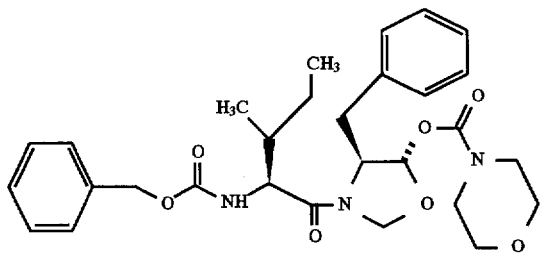

Scheme VII; The title compound prepared in example 29 (0.59 mmol) is O-acylated in a manner analogous to the procedure described in example 3 with 4-morpholinecarbonyl chloride (0.86 mmol), DMAP (10 mg) and triethylamine (1.2 mmol) in methylene chloride (30 mL) to provide the title compound.

EXAMPLE 31

Preparation of [4S-[3(R*),4α,5β]]-[1-[[5-hydroxy-4-[(4-hydroxyphenyl)methyl]3-oxazolidinyl]carbonyl]-3-methylbutyl]-carbamic acid, phenylmethyl ester.

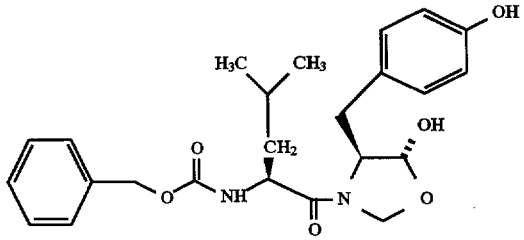

Step A

Scheme VI, step A; N-CBz-Leu-Tyr-OH (11.7 mmol, available from Sigma Chemical Company, St. Louis, Mo. 63178) is cyclized in a manner analogous to the procedure described in example 1, step A with paraformaldehyde (5 g) and p-toluenesulfonic acid monohydrate (500 mg) in benzene to provide the cyclized compound.

Step B

Scheme VI, Step B; The above prepared cyclized compound (4.7 mmol) is reduced in a manner analogous to the procedure described in example 1, step B with DIBAL (10 mmol) in toluene (50 mL) to provide the title compound.

EXAMPLE 32

Preparation of [4S-[3-(R*),4α,5β]]-3-[4-methyl-1-oxo-2-[[(phenylmethoxy)carbonyl]amino]pentyl]-4-[(4hydroxyphenyl)methyl]-5-oxazolidinyl ester, 4morpholinecarboxylic acid.

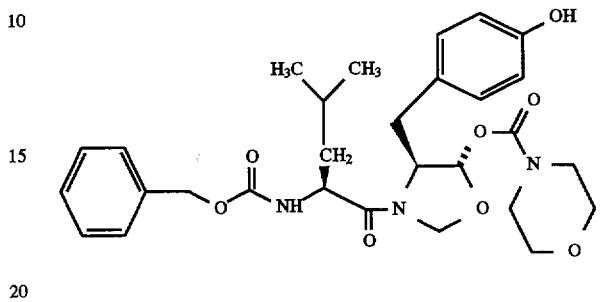

Scheme VII; The title compound prepared in example 31 (0.59 mmol) is O-acylated in a manner analogous to the procedure described in example 3 with 4-morpholinecarbonyl chloride (0.86 mmol), DMAP (10 mg) and triethylamine (1.2 mmol) in methylene chloride (30 mL) to provide the title compound.

EXAMPLE 33

Preparation of

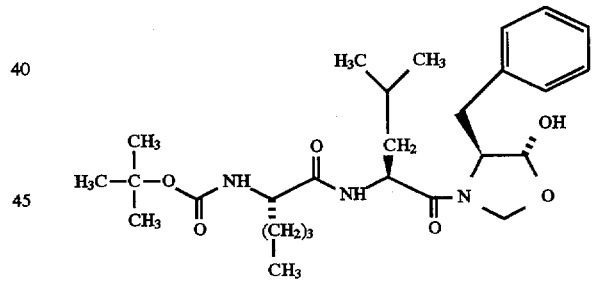

Step A

Scheme VI, step A; N-BOC-norLeu-Leu-Phe-OH (11.7 mmol, available from Sigma Chemical Company, St. Louis, Mo. 63178) is cyclized in a manner analogous to the procedure described in example 1, step A with paraformaldehyde (5 g) and p-toluenesulfonic acid monohydrate (500 mg) in benzene to provide the cyclized compound.

Step B

Scheme VI, Step B; The above prepared cyclized compound (4.7 mmol) is reduced in a manner analogous to the procedure described in example 1, step B with DIBAL (10 mmol) in toluene (50 mL) to provide the title compound.

EXAMPLE 34

Preparation of

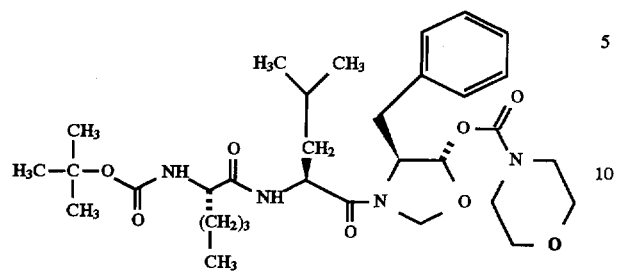

Scheme VII; The title compound prepared in example 33 (0.59 mmol) is O-acylated in a manner analogous to the procedure described in example 3 with 4-morpholinecarbonyl chloride (0.86 mmol), DMAP (10 mg) and triethylamine (1.2 mmol) in methylene chloride (30 mL) to provide the title compound.

EXAMPLE 35

Preparation of

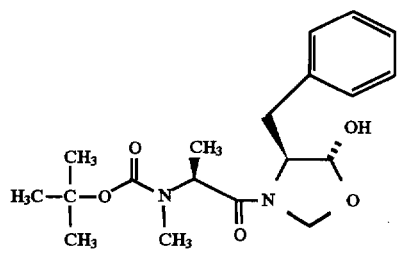

Step A

Scheme III, step B; Dissolve HCl.Phe-OCH$_3$ (4.32 g, 20 mmol) in DMF (20 mL) and cool the solution to 0° C. Add triethylamine (6 mL) and stir for 10 minutes. Then add N-BOC-N-methyl-L-Ala (19.83 mmol, dissolved in 150 mL THF, available from Sigma Chemical Company, St. Louis, Mo. 63178) followed by addition of HOBt (2.83 g, 21 mmol) and EDC (4.0 g, 21 mmol). Stir the reaction for 3 hours at 0° C. and then at room temperature overnight. Concentrate the reaction under vacuum and take up the residue in 1N HCl (100 mL) and extract with ethyl acetate (3×100 mL). Combine the organic extracts, rinse with saturated sodium bicarbonate (100 mL), brine (100 mL), dry over anhydrous magnesium sulfate, pass through a short pad of silica gel and concentrate under vacuum. Purify the residue by flash chromatography (silica gel, hexane/ethyl acetate) to provide the coupled product.

Step B

Scheme III, step C; The above prepared coupled product (14.3 mmol) is deprotected in a manner analogous to the procedure described in example 15, step B with lithium hydroxide monohydrate (16 mmol) in water (100 mL) and THF (100 mL) to provide the acid.

Step C

Scheme VI, step A; The above prepared acid (5.8 mmol) is cyclized in a manner analogous to that described in example 1, step A with paraformaldehyde (4.0 g), p-toluenesulfonic acid monohydrate (200 mg) and 1,2-dichloroethane (200 mL), to provide the cyclized compound after flash chromatography (silica gel, hexane/ethyl acetate).

Step D Scheme VI, step B; The above cyclized compound (4.7 mmol) is reduced in a manner analogous to the procedure described in example 1, step B using DIBAL (10 mmol) in toluene (60 mL) to provide the the title compound.

EXAMPLE 36

Preparation of

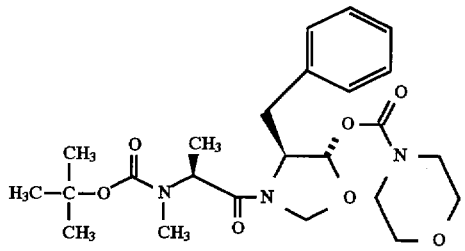

Scheme VII; The title compound prepared in example 35 (0.59 mmol) is O-acylated in a manner analogous to the procedure described in example 3 with 4-morpholinecarbonyl chloride (0.86 mmol), DMAP (10 mg) and triethylamine (1.2 mmol) in methylene chloride (30 mL) to provide the title compound.

EXAMPLE 37

Preparation of

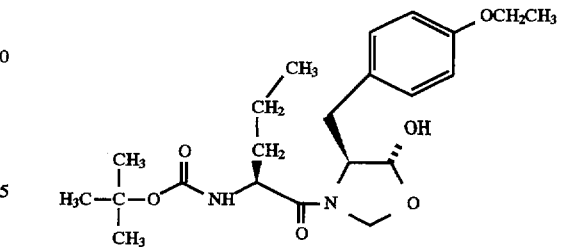

Step A

Treat N-BOC-O-ethyl-L-Tyr-OH (20 mmol, commercially available from Sigma Chemical Company, St. Louis, Mo. 63178) with diazomethane in a manner analogous to the procedure described in example 25, step A to provide the methyl ester (N-BOC-O-ethyl-L-Tyr-OCH$_3$).

Step B

Scheme IV, step B1; The above prepared methyl ester is is deprotected in a manner analogous to the procedure described in example 18, step B with trifluoroacetic acid (10 mL) in methylene chloride (20 mL) to provide the deprotected compound, (O-ethyl-L-Tyr-OCH$_3$).

Step C

Scheme IV, step B2; The above prepared deprotected compound (22 mmol) is coupled with N-BOC- L-norVal (22 mmol dissolved in 130 mL DMF, commercially available from Sigma Chemical Company, St. Louis Mo. 63178) in a manner analogous to the procedure described in example 18, step C with triethylamine (44 mmol), HOBt (22 mmol) and EDC (22 mmol) to provide the coupled compound.

Step D

Scheme IV, step C; The above prepared coupled compound (14.3 mmol) is deprotected in a manner analogous to the procedure described in example 7, step C with lithium hydroxide monohydrate (16 mmol) in water (100 mL) and THF (100 mL) to provide the acid.

Step E

Scheme VI, step A; The above prepared acid (5.8 mmol) is cyclized in a manner analogous to the procedure described in example 1, step A with paraformaldehyde (4.0 g) and p-toluenesulfonic acid monohydrate (200 mg) in 1,2-dichloroethane to provide the cyclized compound.

Step F

Scheme VI, step B; The above prepared cyclized compound (4.7 mmol) is reduced in a manner analogous to the procedure described in example 1, step B with DIBAL (10 mmol) in toluene (60 mL) to provide the title compound.

EXAMPLE 38

Preparation of

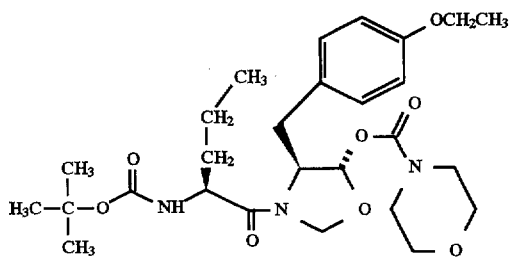

Scheme VII; The title compound prepared in example 37 (0.59 mmol) is O-acylated in a manner analogous to the procedure described in example 3 with 4-morpholinecarbonyl chloride (0.86 mmol), DMAP (10 mg) and triethylamine (1.2 mmol) in methylene chloride (30 mL) to provide the title compound.

EXAMPLE 39

Preparation of [4S-[3(R*),4α,5β]]-[1-[[5-(propionyloxy)-4-(phenylmethyl)-3-oxazolidinyl]carbonyl]-2-methylpropyl]-carbamic acid, phenylmethyl ester (MDL 105,837).

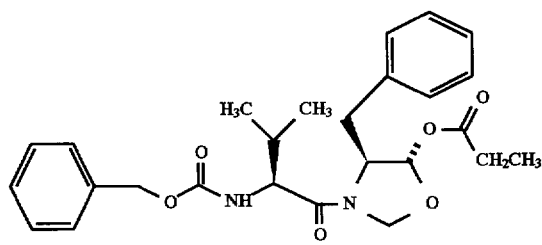

Scheme VII; Dissolve [4S-[3(R*),4α,5β]]-[1-[[5-hydroxy-4-(phenylmethyl)-3-oxazolidinyl]carbonyl]-2-methylpropyl]-carbamic acid, phenylmethyl ester (0.375 g, 0.909 mmol, prepared in example 1) in methylene chloride (9 mL). Add N-methylmorpholine (0.276 g, 2.73 mmol) and propionyl chloride (0.126 g, 1.36 mmol) and stir at room temperature under $N_2$ overnight. Dilute the reaction mixture with additional methylene chloride (40 mL) and wash with 1N HCl (2×25 mL), saturated $NaHCO_3$ (1×25 mL), brine (1×25 mL) and dry over $MgSO_4$. Remove the solvent in vacuo and purify the residue by flash chromatography (silica gel, hexane/ethyl acetate (2:1), loading with methylene chloride) to give the title compound (0.299 g) as a viscous clear, colorless oil. $R_f$=0.56; $[α]^{20}_D$=−47.9 ($CHCl_3$, C=0.514)

EXAMPLE 40

Preparation of [4S-[3(R*),4α,5β]]-[1-[[5-(ethylsuccinyloxy)-4-(phenylmethyl)-3-oxazolidinyl]carbonyl]-2-methylpropyl]-carbamic acid, phenylmethyl ester (MDL 105,608).

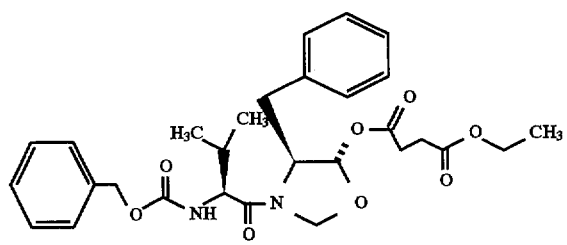

Scheme VII; Dissolve [4S-[3(R*),4α,5β]]-[1-[[5-hydroxy-4-(phenylmethyl)-3-oxazolidinyl]carbonyl]-2-methylpropyl]-carbamic acid, phenylmethyl ester (0.57 g, 1.38 mmol, prepared in example 1), ethyl succinyl chloride (0.45 g, 2.77 mmol) and N-methylmorpholine (0.306 g, 3.04 mmol) in methylene chloride (5.4 mL). Stir the reaction mixture overnight, pour into $H_2O$ and extract with diethyl ether (2×150 mL). Wash the combined extracts with dilute HCl, dilute $NaHCO_3$, $H_2O$ and dry over $Na_2SO_4$. Remove the solvent in vacuo and purify the residue by flash chromatography (silica gel, eluted with 25% ethyl acetate/hexane) to give the title compound (total after pooling of three fractions=468 mg).

EXAMPLE 41

Preparation of [4S-[3(R*),4α,5β]]-[1-[[5-(2-ethylhexanoyl-oxy)-4-(phenylmethyl)-3-oxazolidinyl]carbonyl]-2-methylpropyl]-carbamic acid, phenylmethyl ester (MDL 104,092).

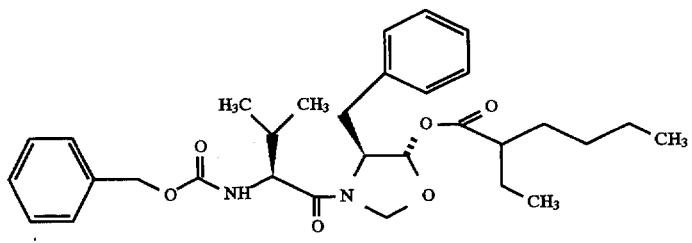

Scheme VII; Dissolve [4S-[3(R*),4α,5β]]-[1-[[5-hydroxy-4-(phenylmethyl)-3-oxazolidinyl]carbonyl]-2-methylpropyl]-carbamic acid, phenylmethyl ester (0.5 g, 1.21 mmol, prepared in example 1), in methylene chloride (5 mL). Add N-methylmorpholine (0.27 g, 2.67 mmol) and 2-ethylhexanoyl chloride (0.39 g, 2.4 mmol) and stir reaction mixture overnight. Pour the reaction mixture into $H_2O$ and extract with diethyl ether (3×50 mL). Wash the combined extracts with dilute HCl, $NaHCO_3$ and dry over $Na_2SO_4$. Remove the solvent in vacuo and purify the residue by flash chromatography (silica gel, eluted with 25% ethyl acetate/hexane) to give the title compound (120 mg).

EXAMPLE 42

Preparation of [4S-[3(R*),4α,5β]]-[1-[[5-(4-methoxyphenyl-acetyloxy)-4-(phenylmethyl)-3-oxazolidinyl]carbonyl]-2-methylpropyl-1]-carbamic acid, phenylmethyl ester (MDL 105,236).

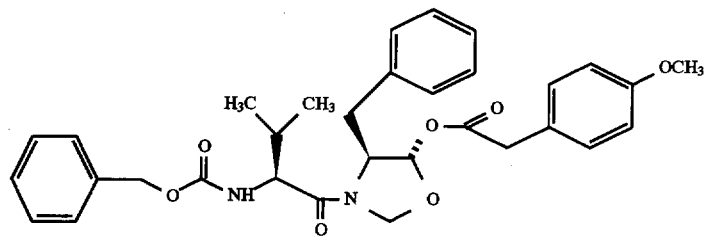

Scheme VII; Dissolve [4S-[3(R*),4α,5β]]-[1-[[5-hydroxy-4-(phenylmethyl)-3-oxazolidinyl]carbonyl]-2-methylpropyl]-carbamic acid, phenylmethyl ester (0.5 g, 1.21 mmol, prepared in example 1), in methylene chloride (5 mL). Add N-methylmorpholine (0.27 g, 2.67 mmol) and 4methoxyphenylacetyl chloride (0.44 g) and stir the reaction mixture overnight. Pour the reaction mixture into $H_2O$ overlayed with diethyl ether. Extract the aqueous layer with additional diethyl ether (2×50 mL) and wash the combied organic extracts with dilute HCl, $NaHCO_3$ and dry over $Na_2SO_4$. Remove the solvent in vacuo and purify the residue by flash chromatography (silica gel, eluted with 25% ethyl acetate/hexane) to give the title compound (580 mg).

One subclass of novel compounds within the scope of the present invention is represented by compounds of formula (I) wherein R is hydrogen, OH, or halogen; $R_1$ is isopropyl, isobutyl, sec-butyl, or methyl; $R_2$ is isobutyl; $R_3$ is hydrogen; $R_4$ and $R_5$ are each independently hydrogen or methyl; $R_6$ is carbobenzyloxy,

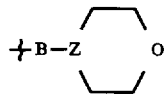

wherein
Z is N or CH; and B is a group of the formulae

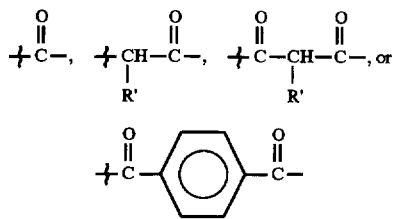

wherein R' is hydrogen or a $C_1$–$C_6$ alkyl group; $R_7$ is hydrogen; m is the integer zero or one and n is the integer zero or one.

Another subclass of novel compounds within the scope of the present invention is represented by compounds of formula (I) wherein R is hydrogen, OH, or halogen; $R_1$ and $R_2$ are each independently $C_1$–$C_4$ alkyl; $R_4$ and $R_5$ are each independently hydrogen or methyl; $R_6$ is carbobenzyloxy; m is zero and n is the integer one.

The following list illustrates some of the compounds according to the present invention:

[4S-[3(R*),4α,5β]]-[1-[[5-hydroxy-4-(phenylmethyl)-3-oxazolidinyl]carbonyl]-2-methylpropyl]carbamic acid, phenylmethyl ester;

[4S-[3(R*),4α,5β]]-[1-[[5-(acetyloxy)-4-(phenylmethyl)-3-oxazolidinyl]carbonyl]-2-methylpropyl]carbamic acid, phenylmethyl ester;

[4S-[3(R*),4α,5β]]-3-[3-methyl-1-oxo-2-[[(phenylmethoxy)carbonyl]amino]butyl]-4-(phenylmethyl)-5-oxazolidinyl ester, 4-morpholinecarboxylic acid;

[4S-[3(R*),4α,5β]]-[1-[[5-hydroxy-4-(phenylmethyl)-3-oxazolidinyl]carbonyl]-2-methylpropyl]methylcarbamic acid, phenylmethyl ester;

[4S-[3(R*),4α,5β]]-[1-[[5-hydroxy-4-(phenylmethyl)-3-oxazolidinyl]carbonyl]-3-methylbutyl]methylcarbamic acid, phenylmethyl ester;

[4S-[3(R*),4α,5β]]-[1-[[5-hydroxy-4-(phenylmethyl)-3-oxazolidinyl]carbonyl]-3-methylbutyl]carbamic acid, phenylmethyl ester;

[4S-[3(R*),4α,5β]]-N-[1-[[5-hydroxy-4-(phenylmethyl)-3-oxazolidinyl]carbonyl]-2-methylpropyl]-4morpholinecarboxamide;

[4S-[4α,5β]]-5-hydroxy-4-(phenylmethyl)-3-oxazolidinecarboxylic acid, phenylmethyl ester;

[4S-[3(R*),4α,5β]]-[1-[[5-(butyryloxy)-4-(phenylmethyl)-3-oxazolidinyl]carbonyl]-2-methylpropyl]carbamic acid, phenylmethyl ester;

[4S-[3(R*),4α,5β]]-[1-[[5-hydroxy-2,2-dimethyl-4-(phenylmethyl)-3-oxazolidinyl]carbonyl]-2-methylpropyl]carbamic acid, phenylmethyl ester;

[4S-[3(R*),4α,5β]]-[1-[[5-(acetyloxy)-2,2-dimethyl-4-(phenylmethyl)-3-oxazolidinyl]carbonyl]-2-methylpropyl]carbamic acid, phenylmethyl ester;

[2R-[2α,3,(S*),4β,5α]]-[1-[[5-hydroxy-2-methyl-4-(phenylmethyl)-3-oxazolidinyl]carbonyl]-2-methylpropyl]carbamic acid, phenylmethyl ester;

[2S-[2α,3,(R*),4α,5β]]-[1-[[5-hydroxy-2-methyl-4-(phenylmethyl)-3-oxazolidinyl]carbonyl]-2-methylpropyl]carbamic acid, phenylmethyl ester;

[2R-[2α,3,(S*),4β,5α]]-[1-[[5-hydroxy-2-(phenylmethyl)-4-(phenylmethyl)-3-oxazolidinyl]carbonyl]-2-methylpropyl]carbamic acid, phenylmethyl ester;

[2S-[2α,3,(R*),4α,5β]]-[1-[[5-hydroxy-2-(phenylmethyl)-4-(phenylmethyl)-3-oxazolidinyl]carbonyl]-2-methylpropyl]carbamic acid, phenylmethyl ester;

[4S-[3(R*),4α,5β]]-[1-[[5-hydroxy-4-[(4hydroxyphenyl)methyl]-3-oxazolidinyl]carbonyl]-2-methylpropyl]carbamic acid, phenylmethyl ester;

[4S-[3(R*),4α,5β]]-1-[[5-hydroxy-4-[(4methoxyphenyl)methyl]-3-oxazolidinyl]carbonyl]-2-methylpropyl] carbamic acid, phenylmethyl ester;

[4S-[3(R*),4α,5β]]-1-[[5-hydroxy-4-[(4-nitrophenyl)methyl]-3-oxazolidinyl]carbonyl]-2-methylpropyl] carbamic acid, phenylmethyl ester;

[4S-[3(R*),4α,5β]]-1-[[4-[(4-aminophenyl)methyl]-5-hydroxy-3-oxazolidinyl]carbonyl]-2-methylpropyl] carbamic acid, phenylmethyl ester;

[4S-[3[R*(1R*,2R*)],4α,5β]]-1-[[[1-[[5-hydroxy-4-(phenylmethyl)-3-oxazolidinyl]carbonyl]-2-methylpropyl]amino]carbonyl]-2-methylbutylcarbamic acid, phenylmethyl ester;

[4S-[3[R*(1R*,2R*)],4α,5β]]-1-[[[1-[[5-(acetyloxy)-4-(phenylmethyl)-3-oxazolidinyl]carbonyl]-2-methylpropyl]amino]carbonyl]-2-methylbutylcarbamic acid, phenylmethyl ester;

[4S-[3[R*(!R*)],4α,5β]]-1-[[[1-[[5-hydroxy-4-(phenylmethyl)-3-oxazolidinyl]carbonyl]-2-methylpropyl]amino]carbonyl]-2-methylpropylcarbamic acid, phenylmethyl ester;

[4S-[3[R*(!R*)],4α,5β]]-1-[[[1-[[5-(acetyloxy)-4-(phenylmethyl)-3-oxazolidinyl]carbonyl]-2-methylpropyl]amino]carbonyl]-2-methylpropylcarbamic acid, phenylmethyl ester;

[4S-[3(R*),4α,5β]]-N-[1-[[5-hydroxy-4-(phenylmethyl)-3oxazolidinyl]carbonyl]-2-methylpropyl]methyl-4-morpholinecarboxamide;

[4S-[3(R*),4α,5β]]-1-[[4-[(4-chlorophenyl)methyl]-5-hydroxy-3-oxazolidinyl]carbonyl]-2-methylpropyl] carbamic acid, phenylmethyl ester;

[4S-[3-(R*),4α,5β]]-3-[3-methyl-1-oxo-2-[[(phenylmethoxy)carbonyl]amino]butyl]-4-[(4-chlorophenyl)methyl]-5-oxazolidinyl ester, 4morpholinecarboxylic acid;

[4S-[3(R*),4α,5β]]-1-[[5-hydroxy-4-(phenylmethyl)-3-oxazolidinyl]carbonyl]-ethyl]carbamic acid, phenylmethyl ester;

[4S-[3(R*),4α,5β]]-3-[1-oxo-2-[[(phenylmethoxy)carbonyl]amino]propyl]-4-(phenylmethyl)-5-oxazolidinyl ester, 4-morpholinecarboxylic acid;

[4S-[3(R*),4α,5β]]-1-[[5-hydroxy-4-(phenylmethyl)-3-oxazolidinyl]carbonyl]-2-methylbutyl]carbamic acid, phenylmethyl ester;

[4S-[3(R*),4α,5β]]-3-[3-methyl-1-oxo-2-[[(phenylmethoxy)carbonyl]amino]pentyl]-4-(phenylmethyl)-5-oxazolidinyl ester, 4-morpholinecarboxylic acid;

[4S-[3(R*),4α,5β]]-1-[[5-hydroxy-4-[(4-hydroxyphenyl)methyl]-3-oxazolidinyl]carbonyl]-3methylbutyl] carbamic acid, phenylmethyl ester;

[4S-[3-(R*),4α,5β]]-3-[4-methyl-1-oxo-2-[[(phenylmethoxy)carbonyl]amino]pentyl]-4-[(4-hydroxyphenyl)methyl]-5-oxazolidinyl ester, 4morpholinecarboxylic acid.

In further embodiments, the present invention provides a method for inhibiting calpain in a patient in need thereof or in treating a patient afflicted with an acute or chronic neurodegenerative disorder comprising the administration thereto of a therapeutically effective amount of a compound of formulae (I). The term "acute or chronic neurodegenerative disorder" refers to diseases or conditions characterized by the inappropriate and detrimental deletion of neurons in the mature adult central nervous system and includes, but is not limited to ischemic stroke (thrombotic or embolic in origin), hemmorhagic stroke and subsequent vascular phemomena, myocardial infarction, neurologic consequences of coronary bypass and grafting operations, head trauma, Alzheimer's Disease, age-associated dementia, vascular dementias, Parkinson's disease, amyotrophic lateral sclerosis, and the like. Compounds of formula (I) which are particularly preferred for the treatment of acute or chronic neurodegenerative disorders include:

[4S-[3(R*),4α,5β]]-1-[[5-hydroxy-4-(phenylmethyl)-3-oxazolidinyl]carbonyl]-2-methylpropyl]carbamic acid, phenylmethyl ester;

[4S-[3(R*),4α,5β]]-1-[[5-(acetyloxy)-4-(phenylmethyl)-3-oxazolidinyl]carbonyl]-2-methylpropyl]carbamic acid, phenylmethyl ester;

[4S-[3(R*),4α,5β]]-3-[3-methyl-1-oxo-2-[[(phenylmethoxy)carbonyl]amino]butyl]-4-(phenylmethyl)-5-oxazolidinyl ester, 4-morpholinecarboxylic acid;

[4S-[3(R*),4α,5β]]-1-[[5-hydroxy-4-(phenylmethyl)-3-oxazolidinyl]carbonyl]-2-methylpropyl]methylcarbamic acid, phenylmethyl ester; and

[4S-[4α,5β]]-5-hydroxy-4-(phenylmethyl)-3-oxazolidinecarboxylic acid, phenylmethyl ester.

As used herein, the term "patient" refers to a warm blooded animal such as a mammal which is afflicted with a particular acute or chronic neurodegenerative disorders. It is understood that guinea pigs, dogs, cats, rats, mice, horses, cattle, sheep, and humans are examples of animals within the scope of the meaning of the term.

The term "therapeutically effective amount" refers to an amount which is effective, upon continuous infusion or upon single or multiple dose administration to the patient, in providing a reduction in the extent of damage associated with acute or chronic neurodegenerative disorders, leading to an improved outcome and/or a delay or prevention of disease progression as compared to outcomes expected in the absence of treatment. The term "therapeutically effective amount" does not necessarily indicate a total elimination or cure of the disease. In determining the therapeutically effective amount or dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances.

A therapeutically effective amount of a compound of formula (I) is expected to vary from about 0.1 milligram per kilogram of body weight per day (mg/kg/day) to about 100 mg/kg/day. Preferred amounts are expected to vary from about 0.5 to about 30 mg/kg/day.

The compounds of this invention are highly potent inhibitors of calpain and cathepsin B. It is believed that the compounds of this invention exert their inhibitory effect through inhibition of the enzyme calpain and thereby delay or prevent acute or chronic neurodegenerative disorders including ischemic stroke (thrombotic or embolic in origin), hemmorhagic stroke and subsequent vascular phemomena, myocardial infarction, neurologic consequences of coronary bypass and grafting operations, head trauma, Alzheimer's Disease, age-associated dementia, vascular dementias, Parkinson's disease, amyotrophic lateral sclerosis, and the like. However, it is understood that the present invention is not limited by any particular theory or proposed mechanism to explain its effectiveness in an end-use application.

In effecting treatment of a patient afflicted with a disease state described above, a compound of formula (I) can be administered in any form or mode which makes the compound bioavailable in effective amounts, including oral and parenteral routes. For example, compounds of formula (I) can be administered orally, subcutaneously, intramuscularly, intravenously, transdermally, intranasally, rectally, topically, and the like. Oral or intravenous administration is generally preferred. One skilled in the art of preparing formulations can readily select the proper form and mode of administration depending upon the particular characteristics of the compound selected for the disease state to be treated, the stage of the disease, and other relevant circumstances. Remington's Pharmaceutical Sciences, 18th Edition, Mack Publishing Co. (1990).

The compounds can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the invention, while effective themselves, may be formulated and administered in the form of their pharmaceutically acceptable salts, such as for example, acid addition salts, for purposes of stability, convenience of crystallization, increased solubility and the like.

In another embodiment, the present invention provides compositions comprising a compound of formula (I) in admixture or otherwise in association with one or more inert carriers. These compositions are useful, for example, as assay standards, as convenient means of making bulk shipments, or as pharmaceutical compositions. An assayable amount of a compound of formulae (I) is an amount which is readily measurable by standard assay procedures and techniques as are well known and appreciated by those skilled in the art. Assayable amounts of a compound of formulae (I) will generally vary from about 0.001% to about 75% of the composition by weight. Inert carriers can be any material which does not degrade or otherwise covalently react with a compound of formulae (I). Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers or excipients.

More particularly, the present invention provides pharmaceutical compositions comprising a therapeutically effective amount of a compound of formulae (I) in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral, parenteral, or topical use and may be administered to the patient in the form of tablets, capsules, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention are prepared so that an oral dosage unit form contains between 5.0–300 milligrams of a compound of the invention.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the compound of the invention.

The compounds of formula (I) of this invention may also be administered topically, and when done so the carrier may suitably comprise a solution, ointment or gel base. The base, for example, may comprise one or more of the following: petrolatum, lanolin, polyethylene glycols, bee wax, mineral oil, diluents such as water and alcohol, and emulsifiers and stabilizers. Topical formulations may contain a concentration of a compound of formula (I) or its pharmaceutical salt from about 0.1 to about 10% w/v (weight per unit volume).

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

The activity of the compounds of this invention to inhibit calpain and/or cathepsin B and thus the usefulness of the compounds of formula (I) to delay or prevent acute or chronic neurodegenerative disorders including ischemic stroke (thrombotic or embolic in origin), hemmorhagic stroke and subsequent vascular phemomena, myocardial infarction, neurologic consequences of coronary bypass and grafting operations, head trauma, Alzheimer's Disease, age-associated dementia, vascular dementias, Parkinson's disease, amyotrophic lateral sclerosis, and the like, can be demonstrated by well-recognized and reliable in vitro and in vivo models.

EXAMPLE 43

In Vitro Assay of Calpain in the Prescence of Calpain Inhibitors

Muscle and erythrocyte calpain were assayed by a fluorometric procedure using t-Boc-Val-Leu-Lys-7-amido-4-methyl-coumarin as the substrate, Sasaki et al., *J. Biol. Chem.* 259, 12489–12494 (1984). The enzyme calpain is commercially available and may be purchased from Sigma. The assay buffer, pH, assay techniques and calculation of the inhibitory constant ($K_i$) are similar to those described by Mehdi et al., *Biochem. Biophys. Res. Commun.* 157, 1117–1123 (1988). Table 2 summarizes the ability of selected compounds of this invention to inhibit calpain.

TABLE 2

In Vitro Calpain Inhibition

| COMPOUND | ENZYME Calpain Ki (M) |
|---|---|
| MDL 104,903 | $3.3 \times 10^{-8}$ |
| MDL 104,860 | $1.45 \times 10^{-6}$ |
| MDL 105,803 | $2.0 \times 10^{-6}$ |
| MDL 105,423 | $2.1 \times 10^{-6}$ |
| MDL 103,821 | $1.3 \times 10^{-6}$ |
| MDL 105,387 | $1.2 \times 10^{-6}$ |
| MDL 105,608 | $7.0 \times 10^{-7}$ |
| MDL 104,092 | $3.0 \times 10^{-7}$ |
| MDL 105,236 | $1.1 \times 10^{-6}$ |

EXAMPLE 44

Neuroprotection In Vivo With MDL 104,903 In a Model of Focal Cerebral Ischemia The efficacy of the compounds of formula (I) to limit neurological damage after ischemic stroke and/or to inhibit calpain in vivo can be demonstrated using accepted focal and global ischemia models, including focal ischemia produced by permanent tandem occlusion of the middle cerebral artery and ipsilateral common carotid artery as illustrated by Hong et al., *Stroke* 25,663–669 (1994); focal ischemia using permanent and/or reversible occlusion of the middle cerebral artery and bilateral common carotid arteries as taught by Bartus et al., *Stroke* 25, 2265–2270 (1994); and global ischemia using reversible occlusion of the common carotid arteries and/or vertebral arteries as disclosed by Lee et al., *Proc. Natl. Acad. Sci.* 88, 7233–7237 (1991).

For example, twelve male spontaneously hypertensive rats were divided into two groups: a vehicle-treated group and a calpain inhibitor-treated groups (MDL 104,903; 4×30 mg/kg cumulative doses). Ischemia was induced by permanent tandem occlusion of the right middle cerebral artery and right common carotid artery. Animals were killed 24 hours after surgery, and quantitative measurements of infarction volumes were performed using standard histological techniques and quantitative image analysis. For rats given 4×30 mg/kg I.V. doses via femoral vein at 2 hour intervals beginning 5 min. after initiation of ischemia, a 20.5% reduction in infarct volume was observed. Results demonstrating reductions in cerebral infarction and edema are illustrated in Table 3 below.

TABLE 3

Effects of MDL 104,903 On Reducing Cerebral Infarct in Rats

| Animal (n = 12) | Brain Volume (mm³) | Infarct Volume (mm³) | Infarct Vol. v. Brain Vol. (%) |
|---|---|---|---|
| A. Vehicle-Treated Group | | | |
| 1 | 1300.76 | 206.44 | 15.87 |
| 2 | 1357.88 | 210.12 | 15.47 |
| 3 | 1298.76 | 207.94 | 16.01 |
| 4 | 1251.60 | 201.06 | 16.06 |
| 5 | 1314.98 | 191.10 | 14.53 |
| 6 | 1336.92 | 214.18 | 16.02 |
| Mean | 1310.15 | 205.14 | 15.66 |
| SEM* | 14.90 | 3.32 | 0.24 |
| B. Inhibitor-Treated Group | | | |
| 7 | 1307.52 | 164.94 | 12.61 |
| 8 | 1309.36 | 185.16 | 14.14 |
| 9 | 1257.24 | 170.84 | 13.59 |
| 10 | 1313.62 | 178.58 | 13.59 |
| 11 | 1333.44 | 134.28 | 10.07 |
| 12 | 1326.46 | 144.92 | 10.93 |
| Mean | 1307.94 | 163.12 | 12.49 |
| SEM* | 10.95 | 8.06 | 0.67 |

C. Comparison of Mean Values and Percentage of Infarct Reduction

| | Brain Volume (mm³) | Infarct Volume (mm³) | Infarct Vol. v. Brain Vol. (%) | % of Reduction |
|---|---|---|---|---|
| Vehicle | 1310.15 | 205.14 | 15.66 | |
| MDL 104,903 | 1307.94 | 163.12 | 12.49 | 20.24 |

*SEM signifies standard error of the mean
*Se signifies standard error of the mean As with any group of structurally related compounds which possesses a particular generic utility, certain groups and configurations are preferred. Preferred compounds of formula (I) include the following groupings.

With respect to the substituent R, compounds of formula (I) wherein R is hydrogen or OH are preferred and hydrogen is particularly preferred.

With respect to the substituents $R_1$ and $R_2$, compounds of formula (I) wherein $R_1$ and $R_2$ are each independently methyl, n-propyl, isopropyl, n-butyl, isobutyl or sec-butyl are preferred and isopropyl is particularly preferred.

As for the substituent $R_3$, compounds of formula (I) wherein $R_3$ is hydrogen are particularly preferred.

As for the substituents $R_4$ and $R_5$, compounds of formula (I) wherein $R_4$ and $R_5$ are each independently hydrogen or methyl are preferred and hydrogen is particularly preferred.

With respect to the substituent $R_6$, compounds of formula (I) wherein $R_6$ is carbobenzyloxy or

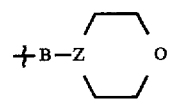

wherein
Z is N or CH; and

B is a group of the formulae $$+\!\!\!\underset{}{\overset{O}{\underset{}{C}}}\!\!-,\quad +\!\!\!\underset{R'}{\overset{O}{\underset{}{CH}}}\!\!-\!\!\overset{O}{\underset{}{C}}\!\!-,\quad +\!\!\!\underset{}{\overset{O}{\underset{}{C}}}\!\!-\!\!\underset{R'}{\overset{}{CH}}\!\!-\!\!\overset{O}{\underset{}{C}}\!\!-, \text{ or}$$

$$+\!\!\!\overset{O}{\underset{}{C}}\!\!-\!\!\!\bigcirc\!\!\!-\!\!\!\overset{O}{\underset{}{C}}\!\!-,$$

wherein R' is hydrogen or a $C_1$–$C_6$ alkyl group, are preferred.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A compound of the formula:

wherein

R and Q are each independently hydrogen, OH, $C_1$–$C_4$ alkyl, $C_1$–$C_4$ alkoxy, $NO_2$, $NH_2$ or halogen;

$R_1$ and $R_2$ are each independently $C_1$–$C_4$ alkyl;

$R_3$ is hydrogen, $C_1$–$C_8$ alkanoyl, $$-\!\!\overset{O}{\underset{}{C}}\!\!-(CH_2)_p\!\!-\!\!\bigcirc\!\!-\!\!Q, \text{ or}$$

$$-\!\!\overset{O}{\underset{}{C}}\!\!-(CH_2)_q\!\!-\!\!\overset{O}{\underset{}{C}}\!\!-\!\!OR_8;$$

$R_4$ and $R_5$ are each independently hydrogen, $C_1$–$C_4$ alkyl or benzyl;

$R_6$ is t-butyloxycarbonyl or carbobenzyloxy;

$R_7$ is hydrogen or methyl;

$R_8$ is $C_1$–$C_4$ alkyl;

m is the integer zero or one;

n is the integer one;

p is the integer zero to three; and q is the integer zero to three;

with the proviso that one of $R_4$ or $R_5$ is hydrogen when the other of $R_4$ or $R_5$ is not hydrogen, methyl or ethyl;

with the further proviso that one of m or n is one when the other of m or n is zero;

or a pharmaceutically acceptable salt thereof.

2. A compound of claim 1 wherein $R_1$ and $R_2$ are each independently methyl, n-propyl, isopropyl, n-butyl, isobutyl or sec-butyl and n is the integer one.

3. A compound of claim 1 wherein $R_3$ is hydrogen.

4. A compound of claim 2 wherein R is hydrogen, $R_4$ is hydrogen, $R_5$ is hydrogen and $R_7$ is hydrogen.

5. A compound of claim 4 wherein $R_6$ is carbobenzyloxy.

6. A compound of claim 1 wherein the compound is [4S-[3(R*),4α,5β]]-[1-[[5-hydroxy-4-(phenylmethyl)-3-oxazolidinyl]carbonyl]-2-methylpropyl]carbamic acid, phenylmethyl ester.

7. A compound of claim 1 wherein the compound is [4S-[3(R*),4α,5β]]-[1-[[5-(acetyloxy)-4-(phenylmethyl)-3-oxazolidinyl]carbonyl]-2-methylpropyl]carbamic acid, phenylmethyl ester.

8. A compound of claim 1 wherein the compound is [4S-[3(R),4α,5β]]-[1-[[5-hydroxy-4-(phenylmethyl)-3-oxazolidinyl]carbonyl]-2-methylpropyl]methylcarbamic acid, phenylmethyl ester.

9. A compound of claim 1 wherein the compound is [4S-[4α,5β]]-5-hydroxy-4-(phenylmethyl)-3-oxazolidinecarboxylic acid, phenylmethyl ester.

10. A compound of claim 1 wherein the compound is [4S-[3(R*),4α,5β]]-[1-[[5-(butyryloxy)-4-(phenylmethyl)-3-oxazolidinyl]carbonyl]-2-methylpropyl]-carbamic acid, phenylmethyl ester.

11. A compound of claim 1 wherein the compound is [4S-[3(R*),4α,5β]]-[1-[[5-(propionyloxy)-4-(phenylmethyl)-3-oxazolidinyl]carbonyl]-2-methylpropyl]-carbamic acid, phenylmethyl ester.

12. A compound of claim 1 wherein the compound is [4S-[3(R*),4α,5β]]-[1-[[5-(ethylsuccinyloxy)-4-(phenylmethyl)-3-oxazolidinyl]carbonyl]-2-methylpropyl]-carbamic acid, phenylmethyl ester.

13. A compound of claim 1 wherein the compound is [4S-[3(R*),4α,5β]]-[1-[[5-(2-ethylhexanoyloxy)-4-(phenylmethyl)-3-oxazolidinyl]carbonyl]-2-methylpropyl]-carbamic acid, phenylmethyl ester.

14. A compound of claim 1 wherein the compound is [4S-[3(R*),4α,5β]]-[1-[[5-(4-methoxyphenyl-acetyloxy)-4-(phenylmethyl)-3-oxazolidinyl]carbonyl]-2-methylpropyl]-carbamic acid, phenylmethyl ester.

15. A composition comprising a compound of claim 1 and an inert carrier.

16. A pharmaceutical composition comprising a therapeutically effective amount of a compound of claim 1 and a pharmaceutically acceptable carrier.

* * * * *

UNITED STATES PATENT AND TRADEMARK OFFICE
CERTIFICATE OF CORRECTION

PATENT NO. : 5,691,368

DATED : November 25, 1997

INVENTOR(s) : Norton P. Peet, et al.

It is certified that error appears in the above-identified patent and that said Letters Patent is hereby corrected as shown below:

At column 3, line 26, the patent reads "$C_1$-C8 alkanoyl" and should read --$C_1$-$C_8$ alkyl--.
At column 7, line 18 the patent reads "Z is as" and should read --wherein Z is as-- .
At column 10, line 41, the patent reads "adamantyloxycaronbyl" and should read --adamantyloxycarbonyl--.
At column 13, line 32, the patent reads "a-carboxyl" and should read --α- carboxyl".
At column 14, line 45, in the structure (9b") the patent reads "$F_6NR_7$" and should read --$R_6NR_7$-- .
At column 20, line 50, the patent reads "reaction then" and should read --reaction is then--.
At column 20, line 53, the patent reads "(60)" and should read -- (60 mL) --.
At column 22, line 63, the patent reads "(300 mg) paraformaldehyde" and should read --(300 mg) and paraformaldehyde-- .
At column 22, line 67, the patent reads "urine: vacuum" and should read --under vacuum-- .
At column 26, line 16, the patent reads "hydroxyl" and should read --hydroxy-- .
At column 27, line 31, the patent reads "3 hours 0°C" and should read --3 hours at 0°C-- .
At column 29, line 37, the patent reads "[b 4S-" and should read --[4S- -- .
At column 30, line 44, the patent reads "methyl-carbamic" and should read --methylpropyl]-carbamic--.
At column 32, line 62, the patent reads "Beat" and should read --Heat-- .
At column 32, line 63, the patent reads "removal a Dean-Stark" and should read --removal of water via a Dean-Stark-- .
At column 32, line 65, the patent reads "residue ethyl" and should read --residue in ethyl--.
At column 33, line 1, the patent reads "layer organic" and should read --layer and organic--.

UNITED STATES PATENT AND TRADEMARK OFFICE
CERTIFICATE OF CORRECTION

PATENT NO. : 5,691,368

DATED : November 25, 1997

INVENTOR(s) : Norton P. Peet, et al.

It is certified that error appears in the above-identified patent and that said Letters Patent is hereby corrected as shown below:

At column 39, line 5, at column 40, line 1, at column 53, lines 18 and 22, reads "(!R*)" and should read --(1R*)-- .

At column 44, line 28, the patent reads "to provide" and should read --to provide the title compound.-- .

At column 51, line 37, the patent reads "combied" and should read --combined--.

At column 60, line 27, claim 8, the patent reads "[4S-[3(R)" and should read --[4S-[3(R*)--.

Signed and Sealed this

Second Day of May, 2000

Attest:

Q. TODD DICKINSON

*Attesting Officer*   *Director of Patents and Trademarks*